United States Patent
Corsini

(10) Patent No.: US 11,491,251 B2
(45) Date of Patent: Nov. 8, 2022

(54) STERILIZATION SYSTEM WITH INTEGRATED INSTRUMENT RECALL CAPABILITIES AND RELATED METHODS

(71) Applicant: Sterisimple Software Inc., Penetanguishene (CA)

(72) Inventor: Sean Andrew Corsini, Penetanguishene (CA)

(73) Assignee: Sterisimple Software Inc., Penetanguishene (CA)

( * ) Notice: Subject to any disclaimer, the term of this patent is extended or adjusted under 35 U.S.C. 154(b) by 705 days.

(21) Appl. No.: 16/433,694

(22) Filed: Jun. 6, 2019

(65) Prior Publication Data

US 2020/0030476 A1    Jan. 30, 2020

Related U.S. Application Data

(60) Provisional application No. 62/702,881, filed on Jul. 24, 2018.

(51) Int. Cl.
| | |
|---|---|
| *A61L 2/24* | (2006.01) |
| *G16H 40/40* | (2018.01) |
| *A61L 2/28* | (2006.01) |
| *A61B 90/96* | (2016.01) |

(52) U.S. Cl.
CPC ............ *A61L 2/24* (2013.01); *A61B 90/96* (2016.02); *A61L 2/28* (2013.01); *G16H 40/40* (2018.01); *A61L 2202/24* (2013.01)

(58) Field of Classification Search
CPC .. A61L 2/24; A61L 2/28; A61B 90/96; G16H 40/40

See application file for complete search history.

(56) References Cited

U.S. PATENT DOCUMENTS

| | | |
|---|---|---|
| 2007/0094303 A1 | 4/2007 | Zwingenberger et al. |
| 2014/0288943 A1 | 9/2014 | Kaniyur-Subbian et al. |

(Continued)

FOREIGN PATENT DOCUMENTS

| | | | |
|---|---|---|---|
| CA | 3012007 | 1/2020 | |
| EP | 2347772 A1 * | 7/2011 | ............... A61L 2/24 |

OTHER PUBLICATIONS

Unknown Author, Sterilog brochure, at least as early as May 17, 2018, 3 pages, http://sterilog.ca/SteriLog_eBrochure.pdf.

(Continued)

*Primary Examiner* — Nathaniel C Chukwurah
(74) *Attorney, Agent, or Firm* — Ridout & Maybee LLP

(57) ABSTRACT

A sterilization system with integrated instrument recall capabilities and related methods is disclosed. In one aspect, the sterilization system is adapted to determine a failed sterilization cycle of a sterilizer in response to failure of a biological indicator test for the sterilizer, identify sterilization cycles to be recalled based on the failed sterilization cycle, identify one or more patients for whom an item in a recalled sterilization cycle was used, and initiate a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

21 Claims, 15 Drawing Sheets

(56) References Cited

U.S. PATENT DOCUMENTS

2016/0235879 A1* 8/2016 Andersson .............. G06F 21/31
2017/0252474 A1* 9/2017 Thompson ................ A61L 2/04

OTHER PUBLICATIONS

Unknown Author, Sterilog homepage, at least as early as Jul. 1, 2018, 2 pages, http://sterilog.ca/.
Unknown Author, SterilWize.ai homepage, at least as early as Jun. 17, 2019, 9 pages, https://www.wize.ai/.
Unknown Author, SterilWize Brochure, at least as early as Jun. 17, 2019, 8 pages, http://wize.ai/images/downloads/SterilWize_Brochure_web.pdf.
Unknown Author, SterilWize comparison, at least as early as Jun. 17, 2019, 1 page, http://wize.ai/images/downloads/SterilWize_comparison_chart.pdf.
Office Action; CA Application No. 3045356 dated Aug. 21, 2020.

\* cited by examiner

STERILIZATION SYSTEM WITH INTEGRATED INSTRUMENT RECALL CAPABILITIES AND RELATED METHODS

RELATED APPLICATION DATA

The present application relates to and claims the benefit of provisional U.S. patent application no. 62/702,881, filed Jul. 24, 2018, the entire contents of which is incorporated herein by reference.

TECHNICAL FIELD

The present disclosure relates to a sterilization system, and in particular, to a sterilization system with instrument recall management.

BACKGROUND

The sterilization of instruments in medical and dental practices is a requirement for public health and safety. A common problem is that sterilization equipment typically provides limited data input and output capabilities if any at all, resulting in manual record keeping by medical or dental staff members which is both time consuming and error prone. Thus, there is a need for a sterilization system with integrated record keeping and data management.

BRIEF DESCRIPTION OF THE DRAWINGS

FIG. 9 is an example search screen of a recall function of the sterilization management application of the sterilization system of the present disclosure for searching by sterilization date.

FIG. 10 is an example search screen of a recall function of the sterilization management application of the sterilization system of the present disclosure for searching by sterilizer.

FIG. 11 is an example search screen of a recall function of the sterilization management application of the sterilization system of the present disclosure for searching by date used.

FIG. 12 is an example search screen of a recall function of the sterilization management application of the sterilization system of the present disclosure for searching by patient name.

DESCRIPTION OF EXAMPLE EMBODIMENTS

Figure 1:
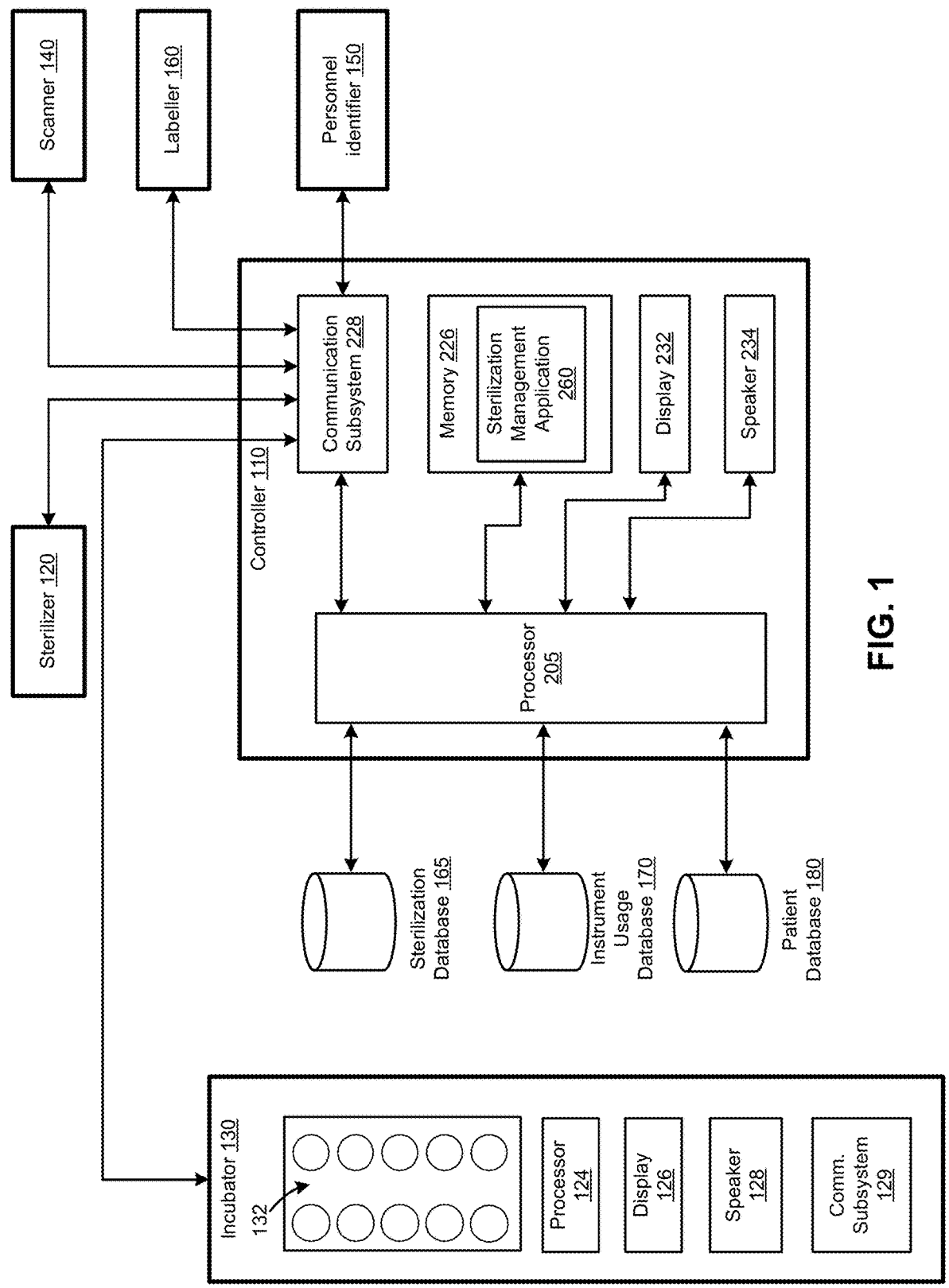
FIG. 1 is a block diagram of a sterilization system in accordance with an example embodiment of the present disclosure.

The present disclosure is made with reference to the accompanying drawings, in which embodiments are shown. However, many different embodiments may be used, and thus the description should not be construed as limited to the embodiments set forth herein. Rather, these embodiments are provided so that this disclosure will be thorough and complete. Like numbers refer to like elements throughout, and prime notation is used to indicate similar elements, operations or steps in alternative embodiments. Separate boxes or illustrated separation of functional elements of illustrated systems and devices does not necessarily require physical separation of such functions, as communication between such elements may occur by way of messaging, function calls, shared memory space, and so on, without any such physical separation. As such, functions need not be implemented in physically or logically separated platforms, although they are illustrated separately for ease of explanation herein. Different devices may have different designs, such that although some devices implement some functions in fixed function hardware, other devices may implement such functions in a programmable processor with code obtained from a machine readable medium. Lastly, elements referred to in the singular may be plural and vice versa, except where indicated otherwise either explicitly or inherently by context.

A sterilization system with integrated instrument recall capabilities and related methods is disclosed. In one aspect, the sterilization system is adapted to determine a failed sterilization cycle of a sterilizer in response to failure of a biological indicator test for the sterilizer, identify sterilization cycles to be recalled based on the failed sterilization cycle, identify one or more patients for whom an item in a recalled sterilization cycle was used, and initiate a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

In accordance with a first aspect of the present disclosure, there is provided a sterilization system. In accordance with one example, there is provided a sterilization system comprising a controller, such as a computer, comprising a processor and a memory coupled to the processor. The sterilization system further comprises one or more sterilizers and a printer coupled to the controller.

The controller may be configured to: receive, by the controller, first sterilization cycle data for the sterilization cycle, the first sterilization cycle data comprising one or more mechanical indicator values for the sterilization cycle; receive, by the controller, second sterilization cycle data for the sterilization cycle; and in response to a determination that mechanical indicators and chemical indicator values for the sterilization cycle match predetermined criteria, generate a sterilization record in accordance with the first sterilization cycle data and second sterilization cycle data, store, by the controller, the sterilization record in a sterilization database, and cause, by the printer, printing of a sterilization label having printed thereon information for the sterilization cycle. The generating, storing and printing may be performed automatically.

The sterilization record may comprise a number of fields, the fields comprising a date of sterilization identifying a date upon which a sterilization cycle was performed, a sterilizer identifier (ID) identifying a sterilizer used in the sterilization cycle, a load type, a number of items sterilized in the load for which all of the chemical indicators matched predetermined criteria and which passed a visual inspection, an ID of a staff member who inspected and verified the mechanical indicators, an ID of a staff member who inspected and verified the chemical indicators as being passed, and an ID of a staff member who inspected and verified the integrity of any pouch or wrapping containing the respective item.

The controller may be further configured to: perform an instrument recall routine for a recalled sterilization cycle in dependence on sterilization cycle parameters for the recalled sterilization cycle in which the controller is configured to: identify one or more patients for whom an item in the recalled sterilization cycle was used by comparing the sterilization cycle parameters for the recalled sterilization cycle to a plurality of records of an instrument usage database; and initiate a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

The records of the instrument usage database may comprise a number of fields, the fields comprising a date of sterilization identifying a date upon which a sterilization cycle was performed, a sterilizer ID identifying a sterilizer used in the sterilization cycle, a load ID identifying a load on the date of sterilization of the sterilization cycle, a number of items sterilized in the load for which all of the chemical indicators matched predetermined criteria and which passed a visual inspection, a patient name identifying a patient for whom an item in the sterilization cycle was used, and a date of use identifying a date upon which the item in the sterilization cycle was used In some examples, the controller is configured to: determine a failed sterilization cycle of a sterilizer in response to failure of a biological indicator test for the sterilizer; and identify sterilization cycles to be recalled based on the failed sterilization cycle.

In some examples, the controller is configured to identify sterilization cycles to be recalled based on the failed sterilization cycle by identifying sterilization cycles performed via the sterilizer since a last successful biological indicator test was obtained for the sterilizer.

In some examples, the controller is configured to automatically, without user intervention, determine the failed sterilization cycle and identify sterilization cycles to be recalled.

In some examples, the controller is configured to, when performing the instrument recall routine for a recalled sterilization cycle: identify unused items from the recalled sterilization cycle by comparing sterilization cycle parameters for the recalled sterilization cycle to a plurality of records of the sterilization database.

In some examples, the sterilization cycle parameters for the recalled sterilization cycle comprise a sterilizer ID and a sterilization date.

In some examples, the determination that the mechanical indicators and chemical indicator values for the sterilization cycle match predetermined criteria is performed automatically by the controller in response to received data for the mechanical indicators and chemical indicators.

In some examples, the controller is configured to: receive data comprising one or more chemical indicators for the sterilization cycle; determine whether the mechanical indicators and chemical indicator values for the sterilization cycle match predetermined criteria.

In some examples, the sterilization system further comprises: an incubator coupled to the controller; wherein the controller is configured to: receive, from the incubator, incubation cycle results for incubation cycles performed by the incubator; determine, from the incubation cycle results, whether an incubation cycles has passed or failed; determine, from an incubation cycle result, that a sterilization cycle has failed in response to a determination that an incubation cycle for a biological indicator has failed.

In some examples, the controller is configured to automatically perform the instrument recall routine for the recalled sterilization cycle in response to the determination that the sterilization cycle has failed.

In some examples, the controller is configured to: receive a patient name identifying a patient for whom a sterilized item was used and a date of use identifying a date upon which the sterilized item was used; receive a sterilizer ID and a sterilization date for the sterilization cycle in which the sterilized item was last sterilized; automatically generate an instrument usage record in accordance with the received patient name and date of use; and automatically store the instrument usage record in an instrument usage database, the instrument usage record comprising a number of fields, the fields comprising a date of sterilization identifying a date upon which a sterilization cycle was performed, a sterilizer identifier (ID) identifying a sterilizer used in the sterilization cycle, a load number identifying a load on the date of sterilization of the sterilization cycle and/or a cycle number identifying the sterilization cycle relative to a reference date, a number of items sterilized in the load for which all of the chemical indicators matched predetermined criteria and which passed a visual inspection, an item type, a patient name identifying a patient for whom an item in the sterilization cycle was used, and a date of use identifying a date upon which the item in the sterilization cycle was used.

In some examples, the sterilizer ID and sterilization date are received via a scanner coupled to the controller, the scanner having extracted the sterilizer ID and sterilization date from a QR code associated with the item.

In some examples, the controller is configured to notify the one or more patients for whom an item in the recalled sterilization cycle was used about the recalled sterilization cycle by: generating an electronic message about recalled sterilization cycle for each patient for whom an item in the recalled sterilization cycle was used; automatically populating each electronic message with a contact address for the respective patient, the contact address being determined from a patient database using the patient name; and sending, via communication module of the controller, each electronic message to the respective contact address.

In some examples, the electronic message includes information about the recalled sterilization cycle and patient instructions.

In some examples, the electronic message is an email message

In some examples, the information printed on the label comprises a QR code.

In some examples, the sterilization record further comprises mechanical indicator status/values and chemical indicator status.

In some examples, the mechanical indicator status/values comprises a minimum and maximum temperature within the sterilizer during the sterilization cycle, a minimum and maximum pressure within the sterilizer during the sterilization cycle, and the duration of the sterilization cycle.

In some examples, the chemical indicator status comprises a Class 1 chemical indicator pass/fail, Class 4 chemical indicator pass/fail/N/A and Class 5 chemical indicator pass/fail.

In some examples, the sterilization record further comprises one or more of a load number and/or cycle number, a load type, and a number of items sterilized in the load for which all of the chemical indicators matched predetermined criteria and which passed a visual inspection.

In accordance with a second aspect of the present disclosure, there is provided a method of performing an instrument recall. In accordance with one example, there is provided a computer-implemented method of performing an instrument recall, wherein the method is performed by a controller comprising a processor and a memory coupled to the processor, the controlled coupled to one or more sterilizers and a printer, the method comprising: receiving first sterilization cycle data for the sterilization cycle, the first sterilization cycle data comprising one or more mechanical indicator values for the sterilization cycle; receiving second sterilization cycle data for the sterilization cycle; and in response to a determination that mechanical indicators and chemical indicator values for the sterilization cycle match predetermined criteria, generating a sterilization record in accordance with the first sterilization cycle data and second sterilization cycle data, storing the sterilization record in a sterilization database, and printing a sterilization label having printed thereon information for sterilization cycle. The generating, storing and printing may be performed automatically.

The sterilization record may comprise a number of fields, the fields comprising a date of sterilization identifying a date upon which a sterilization cycle was performed, a sterilizer identifier (ID) identifying a sterilizer used in the sterilization cycle, a load type, a number of items sterilized in the load for which all of the chemical indicators matched predetermined criteria and which passed a visual inspection, an ID of a staff member who inspected and verified the mechanical indicators, an ID of a staff member who inspected and verified the chemical indicators as being passed, and an ID of a staff member who inspected and verified the integrity of any pouch or wrapping containing the respective item.

The method may further comprise performing an instrument recall routine for an recalled sterilization cycle in dependence on sterilization cycle parameters for the recalled sterilization cycle, performing the instrument recall routine comprising: identifying one or more patients for whom an item in the recalled sterilization cycle was used by comparing sterilization cycle parameters for the recalled sterilization cycle to a plurality of records of an instrument usage database; and initiating a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

Each record of the instrument usage database may comprise a number of fields, wherein the fields of the record of the instrument usage database comprise a date of sterilization identifying a date upon which a sterilization cycle was performed, a sterilizer ID identifying a sterilizer used in the sterilization cycle, a load ID identifying a load on the date of sterilization of the sterilization cycle, a number of items sterilized in the load, a patient name identifying a patient for whom an item in the sterilization cycle was used, and a date of use identifying a date upon which the item in the sterilization cycle was used.

In accordance with a third aspect of the present disclosure, there is provided a method of logging sterilization data. In accordance with one example, there is provided a computer-implemented method of logging sterilization data, wherein the method is performed by a controller comprising a processor and a memory coupled to the processor, the controlled coupled to one or more sterilizers and a printer. The method comprises: receiving, by the processor from the sterilizer, first sterilization cycle data for the sterilization cycle, the first sterilization cycle data comprising one or more mechanical indicator values for the sterilization cycle; receiving, by the processor, second sterilization cycle data for the sterilization cycle; in response to a determination that mechanical indicators and chemical indicators for the sterilization cycle match predetermined criteria, generating, by the processor, a sterilization record in accordance with the first sterilization cycle data and second sterilization cycle data, storing, in the memory, the sterilization record in a sterilization database, the sterilization record comprising a number of fields, the fields comprising a date of sterilization identifying a date upon which a sterilization cycle was performed, a sterilizer identifier (ID) identifying a sterilizer used in the sterilization cycle, a load type, a number of items sterilized in the load for which all of the chemical indicators matched predetermined criteria and which passed a visual inspection, an ID of a staff member who inspected and verified the mechanical indicators, an ID of a staff member who inspected and verified the chemical indicators as being passed, and an ID of a staff member who inspected and verified the integrity of the pouch or wrapping containing the respective item, and causing, by the printer, printing of a sterilization label having printed thereon information for sterilization cycle. The generating, storing and printing may be performed automatically.

In accordance with a further aspect of the present disclosure, there is provided a method, comprising: performing, by a sterilizer, a sterilization cycle for one or more items in the sterilizer, each item containing one or more chemical indicators; in response to a determination that mechanical indicators and chemical indicators for the sterilization cycle match predetermined criteria: generating a sterilization record for the sterilization cycle; storing the sterilization record in a sterilization database in the memory; printing a sterilization label having printed thereon information for the sterilization cycle; and generating a sterilization record for and storing the sterilization record in a sterilization database.

In some examples, the sterilization record comprises number of fields, the fields comprising a date of sterilization identifying a date upon which a sterilization cycle was performed, a sterilizer identifier (ID) identifying a sterilizer used in the sterilization cycle, a number of items sterilized in the load for which all of the chemical indicators matched predetermined criteria and which passed a visual inspection, and a staff member who inspected and verified the mechanical indicators, a staff member who inspected and verified the chemical indicators as being passed, and a staff member who inspected and verified the integrity of the pouch or wrapping containing the respective item.

In some examples, the sterilization record further comprises mechanical indicator status/values and chemical indicator status.

In some examples, the mechanical indicator status/values includes a minimum and maximum temperature within the sterilizer during the sterilization cycle, a minimum and maximum pressure within the sterilizer during the sterilization cycle, and the duration of the sterilization cycle.

In some examples, the chemical indicator status includes a Class 1 chemical indicator pass/fail, Class 4 chemical indicator pass/fail/N/A and Class 5 chemical indicator pass/fail.

In some examples, the sterilization record further comprises one or more of a load number and/or cycle number, a load type, and a number of items sterilized in the load for which all of the chemical indicators matched predetermined criteria and which passed a visual inspection.

In some examples, a biological indicator is included in the sterilizer during the sterilization cycle, the method further comprises: incubating, by an incubator, the biological indicator for a predetermined duration.

In some examples, the method further comprises: quarantining the one or more items until the predetermined duration has expired and a negative result from the incubator is obtained.

In some examples, the sterilization record further comprises a biological indicator test result, the biological indicator test result specifying a biological indicator pass/fall, corresponding well identifier (ID), time of biological indicator pass/fail, and a time when quarantine expired.

In some examples, the method further comprises: receiving a patient name identifying a patient for whom an item in the sterilization cycle was used and a date of use identifying a date upon which the item in the sterilization cycle was used; generating an instrument usage record, and storing the instrument usage record in an instrument usage database.

In some examples, the instrument usage record comprises a number of fields, the fields comprising a date of sterilization identifying a date upon which a sterilization cycle was performed, a sterilizer ID identifying a sterilizer used in the sterilization cycle, a load number identifying a load on the date of sterilization of the sterilization cycle and/or a cycle number identifying the sterilization cycle relative to a reference date, a number of items sterilized in the load, a patient name identifying a patient for whom an item in the sterilization cycle was used, and a date of use identifying a date upon which the item in the sterilization cycle was used.

In some examples, the method further comprises: identifying one or more patients for whom an item in the recalled sterilization cycle was used by comparing sterilization cycle parameters for the recalled sterilization cycle to a plurality of records of an instrument usage database; and initiating a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

In some examples, the method further comprises: receiving sterilization cycle parameters comprising a sterilizer ID and a sterilization date for an recalled sterilization cycle; searching the instrument usage database to identify one or more patients for whom an item in the recalled sterilization cycle was used; notifying the one or more patients for whom an item in the recalled sterilization cycle was used about the recalled sterilization cycle.

In some examples, the method further comprises: performing a new sterilization cycle on the items from the recalled sterilization cycle.

In accordance with yet a further aspect of the present disclosure, there is provided a method of performing an instrument recall using a controller of a sterilization system, comprising: providing, to the controller, an instrument usage database comprising a number of records, each record comprising a number of fields, the fields comprising a date of sterilization identifying a date upon which a sterilization cycle was performed, a sterilizer identifier (ID) identifying a sterilizer used in the sterilization cycle, a load type, a load identifier (ID) identifying a load on the date of sterilization of the sterilization cycle, a number of items sterilized in the load, a patient name identifying a patient for whom an item in the sterilization cycle was used, and a date of use identifying a date upon which the item in the sterilization cycle was used; receiving sterilization cycle parameters comprising a sterilizer (ID) and a sterilization date for an recalled sterilization cycle; searching the instrument usage database to identify one or more patients for whom an item in the recalled sterilization cycle was used; notifying the one or more patients for whom an item in the recalled sterilization cycle was used about the recalled sterilization cycle.

In some examples, the method further comprises: performing a new sterilization cycle on the items from the recalled sterilization cycle.

In accordance with yet a further aspect of the present disclosure, there is provided a method of performing an instrument recall using a controller of a sterilization system, comprising: identifying one or more patients for whom an item in the recalled sterilization cycle was used by comparing sterilization cycle parameters for the recalled sterilization cycle to a plurality of records of an instrument usage database; and initiating a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

In accordance with yet a further aspect of the present disclosure, there is provided a method of performing an instrument recall using a controller of a sterilization system, comprising: providing, to the controller, an instrument usage database comprising a number of records, each record for a sterilization cycle and comprising a number of fields, the number of fields comprising a date field specifying a date of sterilization of the respective sterilization cycle, a sterilizer identifier (ID) identifying a sterilizer used in the respective sterilization cycle, a load identifier (ID) identifying a load on the date of sterilization of the respective sterilization cycle, and a number of items sterilized in the load for which all of the chemical indicators matched predetermined criteria and which passed a visual inspection; receiving, by the controller, recalled sterilization cycle parameters comprising a sterilizer ID and a sterilization date for an recalled sterilization cycle; searching, by the controller, the instrument usage database to identify items sterilized by during the recalled sterilization cycle; and initiating an instrument recall for the identified unused items from the recalled sterilization cycle.

In some examples, the method further comprises: performing a new sterilization cycle on the items from the recalled sterilization cycle.

In accordance with a further aspect of the present disclosure, there is provided a method of performing instrument sterilization using a sterilization system of the present disclosure.

In accordance with other aspects of the present disclosure, there is provided a controller, such as a computer of a sterilization system, comprising a processor and a memory, such as a non-transitory machine readable medium. The non-transitory machine readable medium has tangibly stored thereon executable instructions for execution by the processor that, when executed by the processor, cause the control to perform the methods described above and herein.

In accordance with further aspects of the present disclosure, there is provided a non-transitory machine readable medium having tangibly stored thereon executable instructions for execution by a processor of a controller, such as a computer of a sterilization system. The executable instructions, when executed by the processor, cause the sterilization system to perform the methods described above and herein.

Sterilization System

Reference is first made to FIG. 1 which shows in schematic block diagram form a sterilization system 100 in accordance with one example embodiment of the present disclosure. The sterilization system 100 comprises a controller 110 coupled to a sterilizer 120, an incubator 130, a scanner 140, a personnel identifier 150, a sterilized item labeller 160, a sterilization database 165, an instrument usage database 170 and a patient database 180 by one or a combination of a wired or wireless connection via communication subsystems of the respective devices. The operation of the controller 110 may be controlled by a sterilization management (software) application 260 which may be part of, or interface with, scheduling (software) application (not shown). The scheduling application allows the scheduling of patient appointments and management of patient information. The scheduling application may comprise, or interface with, the patient database 180. The sterilization management application 260, scheduling application, sterilization database 165, instrument usage database 170 and/or patient database 180 may be stored in a memory of the controller 110. The sterilization database 165 and instrument usage database 170 may be combined in some embodiments. Alternatively, at least some of data from the sterilization database 165 may be replicated in the instrument usage database 170.

Although only one controller 110, sterilizer 120, incubator 130, scanner 140, personnel identifier 150 and sterilized item labeller 160 are shown in the embodiment of FIG. 1, multiple units of each type may be provided and communicatively coupled via a local network in other embodiments.

The sterilization system 100 may be provided by an integrated device housing all components in some embodiments. Alternatively, the sterilization system 100 may be provided by separate devices in other embodiments, at least some of which may be placed at different locations in the medical and dental facility (e.g., hospital, private medical and dental practice, etc.), depending on the embodiment. For example, the controller 110 may be located remotely from at least some of the other system components such as the sterilizer 120, incubator 130, a scanner 140, personnel identifier 150, and sterilized item labeller 160 for cloud-based connectivity. In such examples, the controller 110 may communicate with the other system components via one or more communications networks (not shown) such as the Internet. For example, the primary functions of the controller 110 and sterilization management application 260 may be performed by a server (not shown) located remotely from a dental or medical facility in which the sterilizer 120, incubator 130, a scanner 140, personnel identifier 150, and sterilized item labeller 160 are located. The server communicates with a client terminal, such as a personal computer or tablet computer, in the dental or medical facility. The sterilization management application 260 is implemented as a client-server application with the client module being a thin client that receives user data via a graphical user interface (GUI) and device data via the local system components, performs minimal processing on such data before sending to the server for processing. The server receives the data from the client terminal, processes such data, and sends the result to the client terminal for use thereon.

The sterilization database 165 comprises a plurality of records, each record comprising a number of fields. In some embodiments, each record comprises fields for a date of item sterilization, sterilizer ID, load number and/or cycle number, load type, number of sterilized items in the load for which all of the chemical indicators matched predetermined criteria and which passed a visual inspection, mechanical indicator status/values, chemical indicator status, biological indicator test result (if applicable), and the staff member who inspected and verified the mechanical indicators and optionally recorded the mechanical indicators (if not reported directly by the sterilizer), who inspected and verified the chemical indicators as being passed, and who inspected and verified the integrity of the pouch or wrapping containing the sterilized items (if any).

The load number is a count of the number of sterilization cycles for a particular sterilizer on a particular date. The cycle number is a running count of the number of sterilization cycles for a particular sterilizer for all time, and may act as a unique sterilization record ID for a particular sterilizer. The load number and the cycle number are typically incremented by 1 as each sterilization cycle is performed and new sterilization record is added to the sterilization database 165, with the load number being reset to zero each date. One or both of the sterilization date and load number or cycle number (or other sterilization record ID) for a particular sterilizer can be used to uniquely identify a sterilization cycle, for example, during an instrument recall. The load type (e.g., pouched, cassette, special or mixed) may make it easier for staff members to identify items in storage in the event of an instrument recall, as described below. The staff member performing each of the inspection and verification tasks for a given sterilization cycle is typically the same but may vary, depending on the medical or dental practice. Typically, one person per load is responsible for inspecting and verifying the mechanical indicators, chemical indicators, the integrity of the pouch or wrapping containing the sterilized item, and biological indicator.

Each record in the instrument usage database 170 comprises a number of fields. In some embodiments, each record comprises fields for a patient name identifying a patient for whom an item in the sterilization cycle was used, date of use identifying a date upon which the item in the sterilization cycle was used, sterilizer identifier (ID) identifying a sterilizer used in the sterilization cycle, date of item sterilization identifying a date upon which a sterilization cycle was performed for the sterilized item, load number (or ID) identifying a load on the date of sterilization of the sterilization cycle and/or cycle number (or ID) identifying the sterilization cycle relative to a reference date, item type (or load type), and a number of items sterilized in the load for which all of the chemical indicators matched predetermined criteria and which passed a visual inspection. An item type may be determined from a load type of a respective sterilization cycle with each item assigned the load type of the respective sterilization cycle. The records in the instrument usage database 170 may be linked to corresponding records in the sterilization database 165 and patient database 180. The instrument usage database 170 is a searchable database that may be searched in accordance with any parameter, each parameter corresponding to a field of the sterilization records.

The patient database 180 comprises a plurality of patient records, each including a patient name, address, and contact information. The contact information may include a contact address for electronic messages and communications such as, for example, an email address. The patient database may be part of an appointment scheduling system in some embodiments. The patient database 180 is a searchable database that may be searched in accordance with any parameter, each parameter corresponding to a field of the patient records (e.g., patient name, address, and contact information).

The sterilization management application 260 may be used to search the instrument usage database 170 using various parameters, generate reports and to display, save and/or print records. The reports may be saved to a designated location (e.g., database or folder) in a particular file format. The sterilization management application 260 may also be used to schedule and perform a backup of the instrument usage database.

Figure 2:
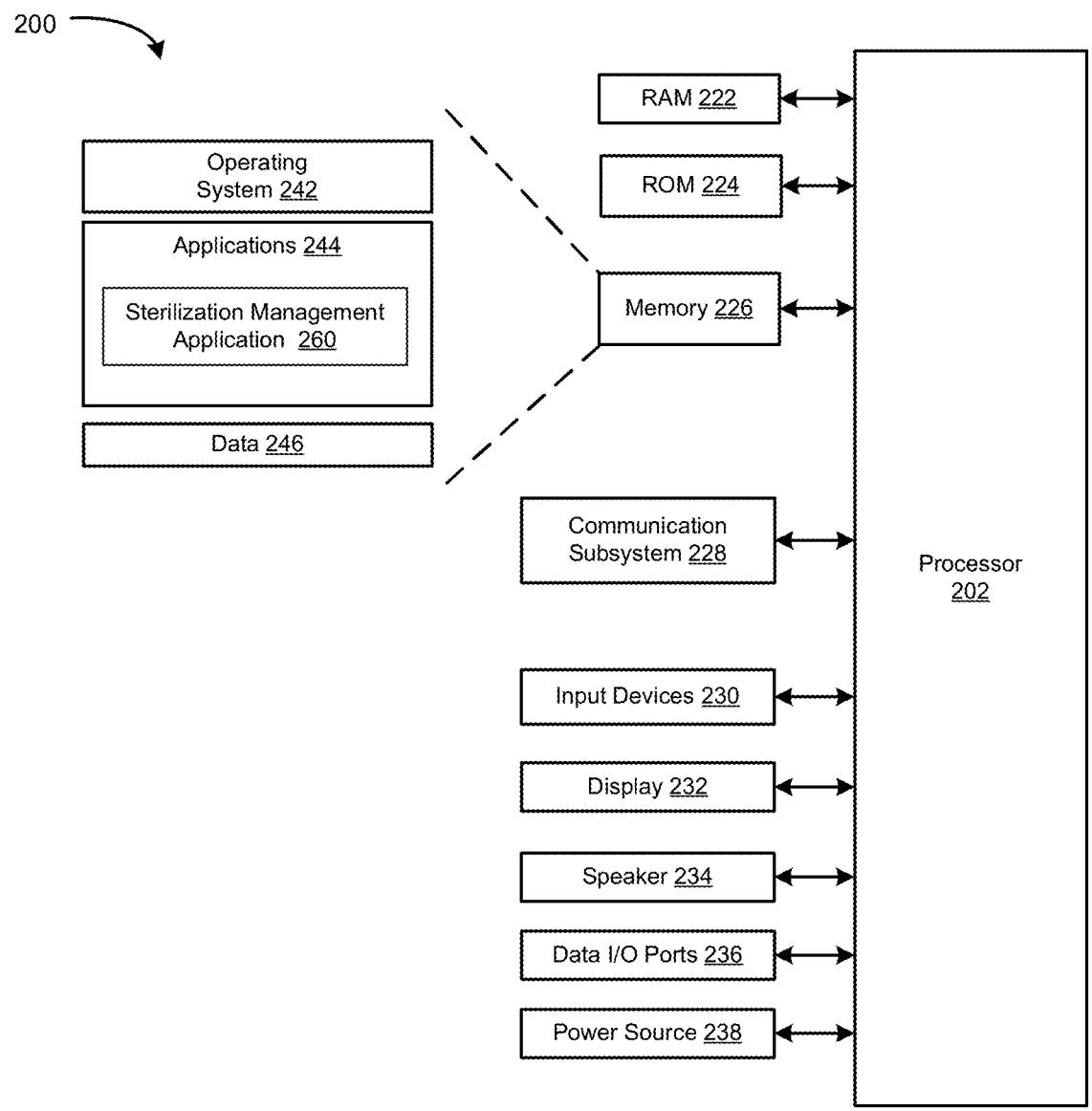
FIG. 2 is a block diagram of a controller of the sterilization system in accordance with one example embodiment of the present disclosure.

The controller 110 comprises at least one processor 202 (FIG. 2) which controls the overall operation of the controller 110 and a memory 226 (FIG. 2). The processor 202 executes the sterilization management application 260, stored in the memory 226, which causes the controller 110 to perform at least a portion of the methods described herein.

The sterilizer 120 is used to sterilize instruments, such as medical or dental instruments. The sterilizer 120 may be an autoclave. The sterilizer accepts one of several load types: pouches, cassettes, mixed, implants or special. A mixed load means one or more cassettes and one or more pouches. Implants are devices placed surgically. Special loads are plastics, which are sterilized at lower temperatures than pouches or cassettes but for a longer duration. Cassettes and special items/loads may be wrapped for the sterilization cycle. Whether such items/loads are wrapped and/or the nature of the wrapping may depend on public health regulations. Implants are wrapped or pouched. A biological indicator, such as a spore test, may be included as part of the contents of each sterilization cycle regardless of the load type. The sterilizer 120 detects and stores one or more mechanical indicators (MIs) during each instrument sterilization (reprocessing) cycle. The results of the MIs (or MI values) may be displayed on a display of the sterilizer 120 and/or output from the sterilizer 120 to the controller 110, depending on the embodiment. The MIs detected and stored by the sterilizer 120 include at least a minimum and maximum temperature within the sterilizer during the sterilization cycle, a minimum and maximum pressure within the sterilizer during the sterilization cycle, and the duration of the sterilization cycle.

The sterilizer 120, in an example embodiment, records a sterilizer name (e.g., A, B, C, etc.), a load type (i.e., pouched, cassette, special or mixed), contents of cycle (e.g., one or more of spore test, wrapped cassettes, pouched instruments, pouched plastics, as applicable), load number (1, 2, 3, etc.), time of cycle start, door check (conformation that door closed, time sterilization started, minimum and maximum temperature during active sterilization, minimum and maximum pressure during active sterilization, duration of active sterilization, any errors (low water, pressure leaks, overpressure, overheating, cycle failures, etc.), time of air drying cycle, time of door opening, Class 5 chemical indicator pass/fail, and time of end of full cycle.

As noted above, a mixed sterilization cycle comprises a mixture of pouches and cassettes, which have the same sterilization requirements (e.g., temperature, pressure and duration).

The load type is entered on the sterilizer 120 by a staff member before each sterilization cycle, and is output to the controller 110 upon completion of the sterilization cycle. An item type may be determined from the load type, with each item assigned the load type for the respective sterilization cycle, or vice versa. An item may contain one or a number of instruments such as a set or kit comprising a predefined set of instruments.

The Class 5 chemical indicator pass/fail may be determined by the sterilizer 120 indirectly by the mechanical indicators rather than directly by the observation and detection of the state of the Class 5 chemical indicator via a corresponding sensor in the sterilizer 120.

The incubator 130 incubates processed (sterilized) biological indicators (BIs), such as spore tests from sterilization cycles, and determines the results of the incubation of the BIs. The incubator 130 contains a number of incubation wells 122 for receiving and incubating biological indicators, sensors (not shown) for each incubation well for sensing a condition of the biological indicators, a processor 124 controlling the overall operation of the incubator 130 and determining the result of the incubation cycle for each incubation well, a display 126 for displaying information (such as, for each incubation well, the respective incubation well number, a time remaining (if any), and the result of the incubation cycle (if any), etc.), a speaker 128 for generating an audible notifications such as sound or tone when an incubation cycle is completed, and a communication subsystem 129 for communicating with other devices such as the controller 110. Each incubation well can be operated independently. When more than one sterilizer 120 is provided, each of incubation well may be assigned to a particular sterilizer 120. The incubator 130 outputs the results of each incubation cycle to the controller 110 which stores the incubator cycle results, for example, in the sterilization database 165, as described in more detail below.

The incubation wells are typically configured for either processed BIs or unprocessed BIs (known as controls). For example, in an incubator 130 having 10 incubation wells, incubation wells no. 5 and 10 may be configured for controls whereas the remaining incubation wells may be configured for processed BIs. Processed (sterilized) BIs may require activation before incubation, depending on the incubator 130. The activation of BIs typically comprises combining spores and a growth media within a growth chamber in the BI.

Each day that a particular sterilizer 120 is used, a BI is sterilized in the sterilizer 120 and incubated in the incubator 130. Typically, the BI is tested (i.e., sterilized and incubated) at the start of the day in the first sterilization cycle for the particular sterilizer 120. The first sterilization cycle may include instruments. The load number and/or cycle number may be adjusted to avoid including the BI test sterilization cycle in the respective load and/or cycle counts. Typically, for second and subsequent sterilization cycles in a given day, no BI is included in the load and no BI test is performed provided a negative BI result was obtained in an earlier sterilization cycle for which a positive BI control result was also obtained unless the load type or contents requires a BI in accordance with public health regulations (e.g., the load includes an implant).

The BI is placed in a challenge pack or process challenge device (PCD) during the sterilization along with a Class V chemical indicator. The PCD is an enclosure or housing configured to protect the spores in the spore vial of the BI, making the spores more difficult to kill in the sterilizer 120. The PCD may be placed within the sterilizer 120 with instruments, possibly over packed with instruments to make the spores even more difficult to kill in the sterilizer 120. Typically, all BIs used in a given day in a given facility from the same lot. A lot of BIs is set of BIs having a common source and expiry date. Each lot of BI is individually packaged and identified by a lot number or code.

The incubation cycle results are detected by the incubator 130 and may be output to the controller 110, which automatically detects the results (pass or fail) in accordance with the output from the incubator 130, for example, via the sterilization management application 260. A negative result from the incubator 130 for a processed BI indicates that growth of the spores in the processed BI was not detected by the incubator 130 and a successful sterilization process. The output of a negative result will only be generated by the incubator 130 after the end of the incubation cycle, and is output to the controller 110. A positive result from the incubator 130 for a processed BI indicates that growth of the spores in the processed BI was detected by the incubator 130 and a failure in the sterilization process. The output of a positive result will typically be generated by the incubator 130 in real-time or near real-time, i.e. immediately after the spore growth and/or sterilization cycle failure is detected, and is output to the controller 110.

A positive result typically requires that all items in the affected sterilization cycle be re-sterilized and may trigger an instrument recall to be initiated depending on public health regulations and settings of the controller 110 of the sterilization system 100. An example of an instrument recall is described below. An instrument recall will cover all items sterilized since the last successful BI test, i.e., last negative BI result, for the corresponding sterilizer 120. In some examples, a second BI may be tested (i.e., sterilized and incubated) and detection of a second positive result may be required before an instrument recall is initiated depending on public health regulations and settings of the controller 110 of the sterilization system 100. In such examples, an instrument recall is initiated only if the second BI test is also positive. If the second BI test is negative, an instrument recall is not initiated.

Each day that a sterilizer 120 is used, i.e. each day that a processed BI is incubated, an unprocessed (unsterilized) BI from each lot from which a processed BI is used is activated and incubated as a BI control. The BI control is typically tested at the start of the day before or with one or more processed (sterilized) BIs, for example, in the first sterilization cycle of the day for the various sterilizers 120.

The incubation period for the processed BIs and the control (i.e., unprocessed BI) may be, for example, 24 minutes to 180 minutes, depending on the BI and/or incubator 130. The incubation period is the same for each type of BI whether processed or unprocessed. Sterilized items for which a negative BI result (i.e., a successful sterilization process) has been obtained are quarantined until the results of the daily control test are available and a positive result for the BI control is determined. Typically, for second and subsequent sterilization cycles in a given day, no BI is included in the load and no BI test is performed provided a negative BI result was obtained in an earlier sterilization cycle for which a positive BI control result was also obtained unless the load type or contents requires a BI in accordance with public health regulations (e.g., the load includes an implant). Public health regulations typically require that each cycle containing an implant includes a BI. While a sterilized item is in quarantine, it is securely stored and cannot be used.

Each control provides a positive control that tests the viability of the spores of each lot of BIs. Because the BI used for the control is unprocessed (unsterilized), growth of spores within the BI should be detected at the end of the incubation period. A positive result from an unprocessed BI (BI control) indicates a growth of spores in the BI control, and validates negative results from processed BIs from the same lot as the unprocessed BI (BI control) on the same date. In other words, a positive result for a BI control indicates a successful sterilization cycle for sterilization cycles having negative results from processed BIs (i.e., no growth) from the same lot on the same date. A negative result from an unprocessed BI, also known as a BI control failure, indicates a lack of growth of spores in the control, and invalidates the results of any negative results from processed BIs (i.e., BI tests) from the same lot as the unprocessed BI (BI control) that failed the BI control test on the same date. The invalidated results consequently invalidate any corresponding successful sterilization cycles, i.e., all successful sterilization cycles in having a processed BI (i.e., BI tests) from the same lot as the unprocessed BI (BI control) that failed the BI control test on the same date. Each item in an invalidated sterilization cycle is considered non-sterile and must be re-sterilized. The BI control failure is detected by the incubator 130 and may be output to the controller 110, which automatically detects the BI control failure.

If the result of the BI control test is negative, a second BI control test is performed using a different unprocessed BI from the same lot. If the result of the second BI control test is also negative, the lot of BIs corresponding is safely discarded. A further BI control test is performed using an unprocessed BI from a different lot. This process is repeated until a positive BI control test is obtained. Once a positive BI control test is obtained, a new BI test is performed for each sterilizer 120. Items from all invalidated sterilization cycles are then re-sterilized. One or more items may be included in the sterilization cycle for the sterilizers 120.

The scanner 140 may also be used to scan processed items to determine a state of one or more chemical indicators (CIs) used to monitor the presence or attainment of one or more of the parameters required for a successful sterilization process. The state of the chemical indicators is typically pass or fail. However, for chemical indicators on the exterior of a pouch or wrapping, such as Class IV, a not available (N/A) may be acceptable for external inspection because it is not visible provided that when the pouch or wrapping is removed prior to use, the status of the chemical indicator is inspected and the instrument(s) in the pouch or wrapping are only used if the chemical indicator has a passed state upon inspection. If not, the sterilization cycle is considered failed and the instrument(s) in the pouch or wrapping are re-sterilized. The chemical indicators which may be scanned include, but are not limited to, one or more of a Class 1, Class 4, and Class 5 chemical indicators. The sterilization management application 260 may allow data entry of the chemical indicators from a staff member in addition to, or instead of, using input from the scanner 140.

A Class 1 chemical indicator is a process indicator applied to the outside of an item to be sterilized (e.g., pouch, cassette or special item). It is designed to change color in response to one critical variable, usually temperature, indicating that the item has been directly exposed to the sterilization process. The Class 1 chemical indicator can be used to distinguish between processed and unprocessed items.

A Class 4 chemical indicator is a multi-parameter indicator placed on the inside of an item to be sterilized (e.g., sterilization pouch), and is designed to change color in response to two or more of the critical variables, usually time and temperature or time, temperature or steam, indicating that the item has been directly exposed to the chosen variables during the sterilization process.

Figure 18:
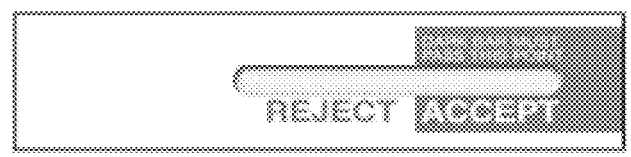
FIG. 18 is a schematic block diagram of a Class 5 chemical indicator in various states.
Figure 18:
Figure 18:
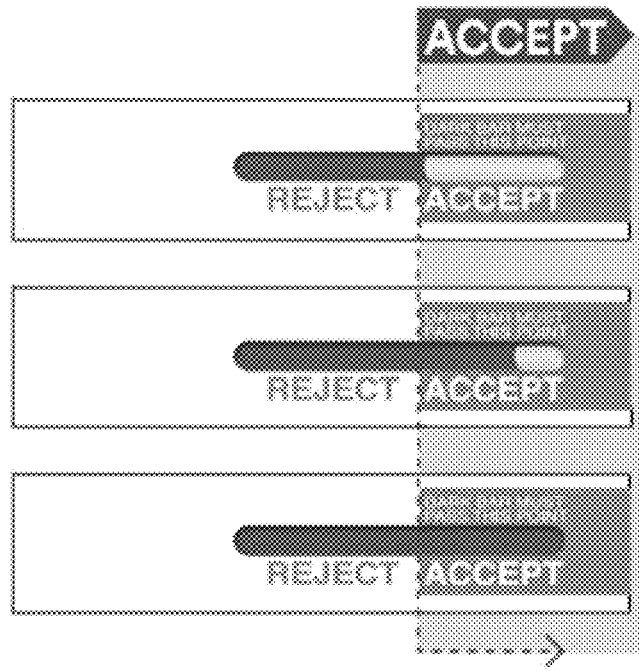
Figure 18:
Figure 18:
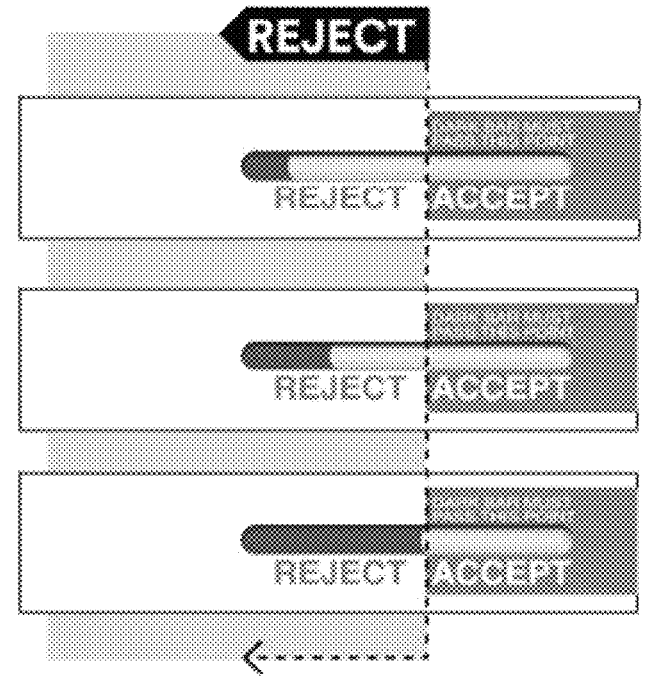
Figure 19:
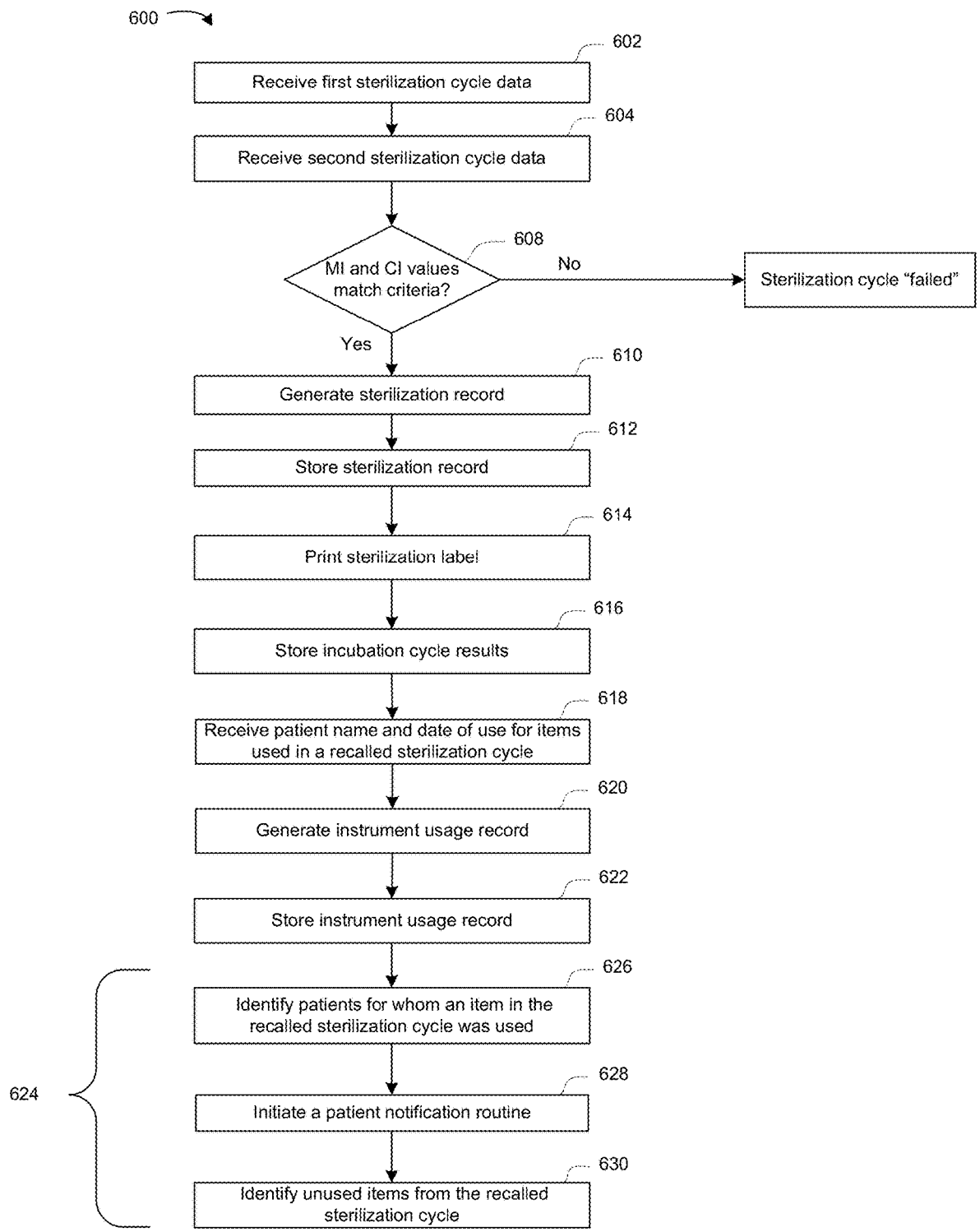
FIG. 19 is a flowchart illustrating a method of performing an instrument sterilization and recall in accordance with one example embodiment of the present disclosure.

A Class 5 chemical indicator is an integrating integrator placed on the inside of an item to be sterilized. It is designed to react to all critical variables and to correlate to biological indicators (BIs). A color change indicates that the item has been directly exposed to the chosen variables during the sterilization process. In some embodiments, a color bar is used to identify the color change. An example of a color bar is shown in FIG. 18. The color bar moves from a "Reject" region to an "Accept" region during sterilization. The color bar must be in the Accept region to be considered a pass. If the color bar is in the Reject region or on the border, it is considered a fail. FIG. 18 shows three examples of the color bar reaching the Accept region indicating that the necessary conditions for sterilization have been met. FIG. 18 also shows three examples of color bar in the Reject Accept region indicating that the necessary conditions for sterilization have not been met. The sterilization cycle should be repeated and the cause of the sterilization failure should be investigated.

The scanner 140 may be used to scan (read) sterilization data on sterilization labels, such as bar codes or QR codes, when a sterilized item is used during a medical or dental procedure, as described more fully below. This allows the sterilizer ID and sterilization date of the associated with a sterilized item being used to be automatically logged. Alternatively, a dedicated bar code/QR code reader may be used to scan bar codes/QR codes instead of the scanner 140.

The personnel identifier 150 is used to identify staff members using one or more technical factors (e.g., smartcard or smart tag, which may be embedded in a wristband or other wearable device) and/or one or more biometric factors (e.g., facial recognition or fingerprint scanner). The personnel identifier 150 may be based on RFID or NFC (near-field communication) or other similar technology. The personnel identifier 150 may comprise one or more of an identification card (smartcard) reader, facial detector, iris scanner, or fingerprint (or thumbprint) scanner. The facial detector, iris scanner and/or fingerprint scanner may be a standalone, dedicated device or a general purpose camera or scanner with specialized software. A facial detector or iris scanner may be preferred in environments in which gloves are worn by staff members because these detectors do not require the removal of gloves. The personnel identifier 150 may be used, in combination with the controller 110, to automatically identify a staff member using the sterilization management application 260 at a given time. Alternatively, the staff member may be identified by login status on the controller 110 or may be selected from a GUI of the sterilization management application 260, for example via a selection box of a data entry screen.

The sterilized item labeller 160 may be a label maker or a printer (e.g., laser printer, inkjet printer, thermal printer, etc.) configured for printing labels. The sterilized item labeller 160 is configured to print labels at the end of each sterilization cycle for each sterilized item (e.g., pouch, cassette or special item) that was sterilized in that sterilization cycle, either automatically or manually. The sterilized item labeller 160 may automatically print the sterilization labels at the end of a successful sterilization cycle for each sterilized item that was sterilized in that sterilization cycle when the CI results have been verified. The CI results may be verified in the sterilization management application 260 via user interaction with a corresponding GUI element, such as clicking or selecting a button or selecting a corresponding value of a drop-down box. In some embodiments, a button or other GUI element may be provided for selection by a user in response to verifying the CI results, the selection of the button causing the printing of the sterilization labels. The sterilized item labeller 160 may also allow users to manually print sterilization labels if desired, for example, because a sterilization label was lost or damaged.

The sterilized item labeller 160 may be mounted to a counter-top, stand or wall. The sterilized item labeller 160 may be coupled to a sensor (not shown) such as a mechanical switch, button, proximity sensor, optical sensor which, when a sterilized item or other object is detected by the sensor, causes the sterilized item labeller 160 to print the sterilization labels for the most recent successful sterilization cycle.

The sterilization label is typically a peelable, adhesive-backed label that may be easily peeled away from its backing and adhered to the respective sterilized item. The sterilization label has printed therein sterilization data in the form of text that specifies at least the following:
  date of sterilization;
  sterilizer name (i.e., the unit which sterilized the item);
  load number;
  a staff member who inspected and verified the mechanical indicators and optionally recorded the mechanical indicators (if not reported directly by the sterilizer);
  a staff member who inspected and verified the chemical indicators as being passed; and
  a staff member who inspected and verified the integrity of the pouch or wrapping containing the sterilized item (if any).
The staff member is identified by an identifier (ID), which may be a proper name, initials, employee number or other suitable identifier that uniquely identifies the staff member. The staff member performing each of the above-noted tasks for a given sterilization cycle may be the same or vary, depending on the medical or dental practice and/or staffing. When the staff member perform the above-noted tasks is the same, a single staff member ID may be provided.

Figure 16:
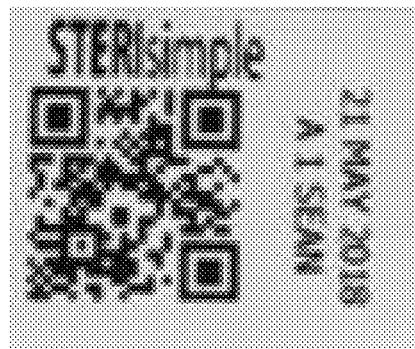
FIG. 16 is an example QR code generated by example embodiments of the s sterilization system of the present disclosure.

The sterilization label may comprise a Quick Response (QR) code label in addition text in some embodiments. The QR code may be generated by the printer 130 or the sterilization management application 260 of the controller 110. A label comprising printed text and a QR code may be relatively small, for example approximately 2.5 cm (1 inch) square, substantially smaller than handwritten labels. An example sterilization label with QR code printed by the sterilized item labeller 160 is shown in FIG. 16. The QR code may encode information additional to the text information such as one or more of the load type, the number of items sterilized in the load for which all of the chemical indicators matched predetermined criteria and which passed a visual inspection, and the load number and/or cycle number. Alternatively, a standard bar code could be used instead of a QR code. In yet other embodiments, the sterilization label may include an RFID (radio-frequency identification) tag in addition to, or instead of, the QR code/bar code. The RFID tag provides a smart tag or smart label containing the same or similar information as the QR code/bar code and is encoded by an RFID encoder (not shown) coupled to the controller 110. The RFID tag may be based on near field communication (NFC) or other suitable communication protocol.

The above-described sterilization system 100 is provided for the purpose of illustration only. The above-described sterilization system 100 is directed to one possible configuration of a multitude of possible configurations. Suitable variations of the sterilization system will be understood to a person of skill in the art and are intended to fall within the scope of the present disclosure. The teachings of the present disclosure are flexible and capable of being operated in various different environments without compromising any major functionality. In some embodiments, the system includes multiple components distributed among a plurality of computing devices. One or more components may be in the form of machine-executable instructions embodied in a machine-readable medium.

Reference is next made to FIG. 2 which illustrates in simplified block diagram form the controller 110 in accordance with one example embodiment of the present disclosure. The controller 110 may be a desktop, laptop or tablet computer in some embodiments. The controller 110 comprises the processor 202 (such as a microprocessor) which controls the overall operation of the controller 110. The processor 202 is coupled to a plurality of components via a communication bus (not shown) which provides a communication path between the components and the processor 202. The processor 202 is coupled to RAM 222, ROM 224, persistent (non-volatile) memory 226 such as flash memory, and a communication module 228 for wired and/or wireless communications over a communications network. The communication module 228 may comprise one or more wireless transceivers including, but not limited to, a Bluetooth® transceiver or other short-range wireless transceiver, a Wi-Fi or other WLAN transceiver for communicating with a WLAN via a WLAN access point (AP), or a cellular transceivers for communicating with a radio access network (e.g., cellular network).

The controller 110 comprises input devices 230 such as a keyboard and mouse or touchscreen, and output devices comprising a display 232 and a speaker 234. When the input devices include a touchscreen, the display 132 and the touchscreen may be provided by the same component. The controller 110 also comprises various data input/output (I/O) ports 236, such as serial data port (e.g., USB data port), and a power source 238.

Operating system software 242 executed by the processor 202 is stored in the persistent memory 226 but may be stored in other types of memory devices, such as ROM 224 or similar storage element. A number of applications 244 executed by the processor 202 are also stored in the persistent memory 226, including the sterilization management application 260. The memory 226 also stores a variety of data 246. The data 246 may comprise user data comprising user preferences, settings and possibly biometric data about the user for authentication and/or identification, a download cache comprising data downloaded via the communication module 228, and saved files. System software, software modules, specific device applications, or parts thereof, may be temporarily loaded into a volatile store, such as RAM 222, which is used for storing runtime data variables and other types of data or information. Communication signals received by the controller 110 may also be stored in RAM 222. Although specific functions are described for various types of memory, this is merely one example, and a different assignment of functions to types of memory may be used in other embodiments.

Figure 3A:
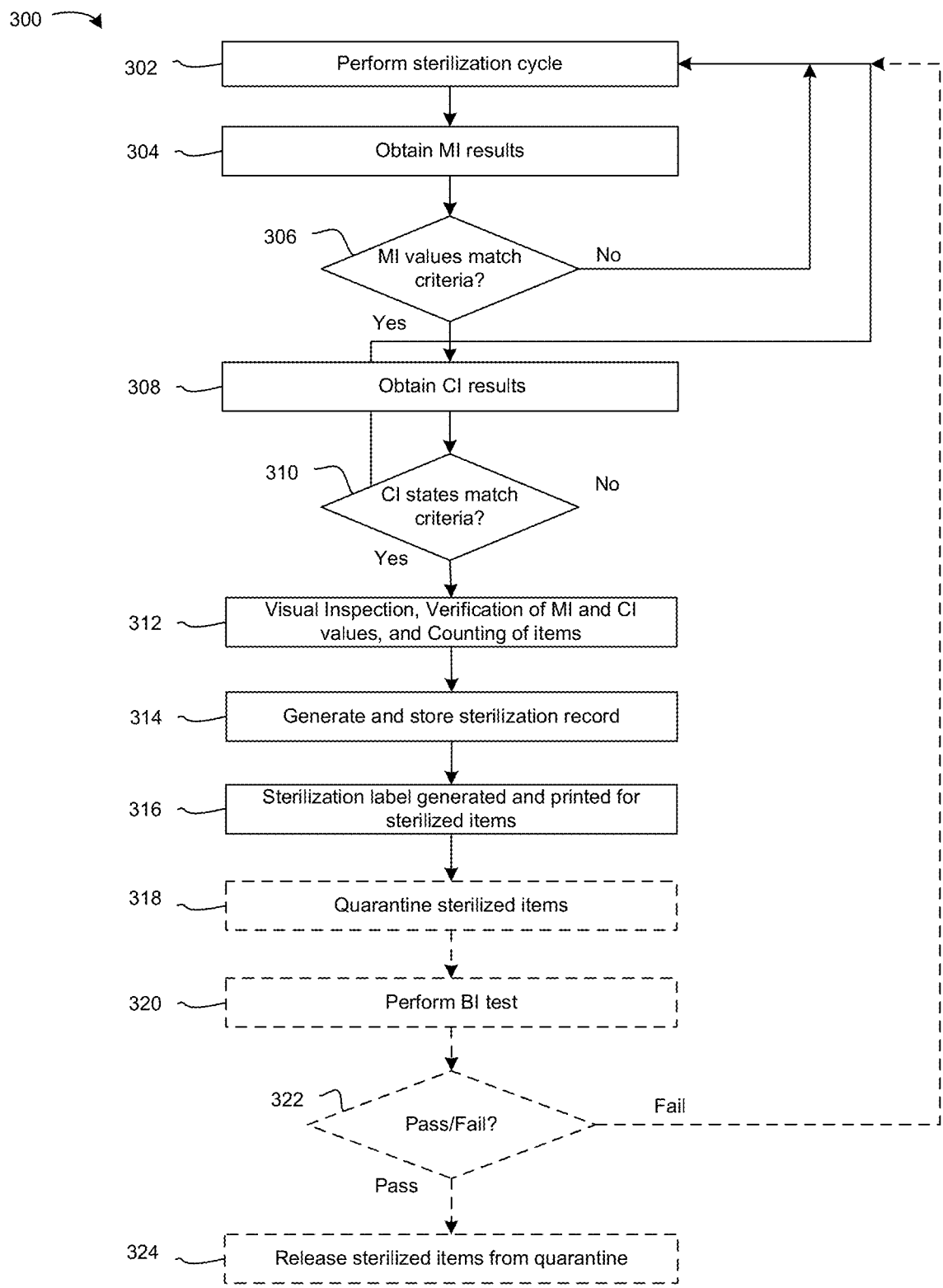
FIG. 3A is a flowchart illustrating a method of performing instrument sterilization using the sterilization system of FIG. 1 in accordance with one example embodiment of the present disclosure.

Referring next to FIG. 3A, a method 300 of performing instrument sterilization using the sterilization system of the present disclosure in accordance with one example embodiment of the present disclosure will be described. At least some of the method 300 may be performed by the controller 110, for example, by the processor 202, or other computing device. The operations may be performed in a differing order, or operations may be added, deleted, or modified in other embodiments.

At operation 302, a sterilization cycle is performed on one or more items by the sterilizer 120 of the sterilization system 100. Each item in the sterilizer 120 to be sterilized has at least one chemical indicator on or in its pouch or wrapping. In some embodiments, a Class I chemical indicator is located on pouch or wrapping, a Class IV chemical indicator is located in the wrapping, and a Class V chemical indicator in the sterilizer 120 with the items to be sterilized but not attached to any particular item. A biological indicator may also be included in the sterilization cycle with the items to be sterilized, for example, because the sterilization cycle is the first of the day or the first after a failed or invalidated sterilization cycle or the load type. At operation 304, the controller 110 receives data output from the sterilizer 120, including mechanical indicator results, at the completion of the sterilization cycle. The MI results include at least a minimum and maximum temperature within the sterilizer during the sterilization cycle, a minimum and maximum pressure within the sterilizer during the sterilization cycle, and the duration of the sterilization cycle.

The MI results are displayed in the GUI of the sterilization management application 260 presented on the display 232 for inspection and verification by a staff member, and are stored within a sterilization record for the sterilization cycle in the sterilization database 165 and instrument usage database 170. The MI results may also be displayed on a display of the sterilizer 120 in response to the required input via the user interface of the sterilizer 120.

At operation 306, it is determined whether the MI values match one or more predetermined criteria, which may vary based on the relevant public health authority. If the MI values do not match the predetermined criteria, the sterilization cycle has failed and must be repeated. If the MI values match the predetermined criteria, the sterilization cycle was successful, and operations proceed to operation 308. In some examples, the predetermined criteria may comprise a minimum and maximum temperature within the sterilizer during the sterilization cycle, a minimum and maximum pressure within the sterilizer during the sterilization cycle, and the duration of the sterilization cycle. In other embodiments, the predetermined criteria may further comprise a condition that no errors were detected by the sterilizer 120 during the sterilization cycle. In other embodiments, the sterilization conditions (e.g., minimum and maximum temperature within the sterilizer during the sterilization cycle, minimum and maximum pressure within the sterilizer during the sterilization cycle, and the duration of the sterilization cycle) may be merely recorded.

At operation 308, all chemical indicators for each sterilized item are evaluated. The chemical indicators may be scanned by the scanner 140, with the output of the scanner 140 being sent to, and received by, the controller 110. This step may be omitted in some embodiments depending on the type of CIs and/or the capabilities of the sterilizer 120. For example, if a Class 5 chemical indicator was used in the sterilization cycle, the status of the Class 5 chemical indicator may be provided directly to the controller 110 by the sterilizer 120. Alternatively, if the sterilizer 120 is not configured to report the status of the Class 5 chemical indicator to the controller 110 or if other chemical indicators are used, i.e. Class 1 or Class 4, the scanner 140 may be used to scan the processed items. The scanner 140, or the controller 110, applies object recognition techniques to determine a state of the chemical indicators. The applied object recognition techniques are pre-trained based on sample images of unprocessed CIs, processed and passed, and processed and failed images, for example, using machine learning/artificial intelligence. Alternatively, in other embodiments the state of the CIs may be determined from inspection by a staff member and added manually to the sterilization management application 260.

At operation 310, it is determined whether the CI states (or statuses) match one or more predetermined criteria, which may vary based on the relevant public health authority. This operation is performed by the controller 110 in embodiments in which the scanner 140 is used to evaluate the CI states. If the CI states do not match the predetermined criteria, the sterilization cycle has failed and must be repeated. When the sterilization cycle fails, each item in the load is considered non-sterile and must be re-sterilized. If the CI states match the predetermined criteria, the sterilization cycle was successful, and operations proceed to operation 312.

Figure 6:
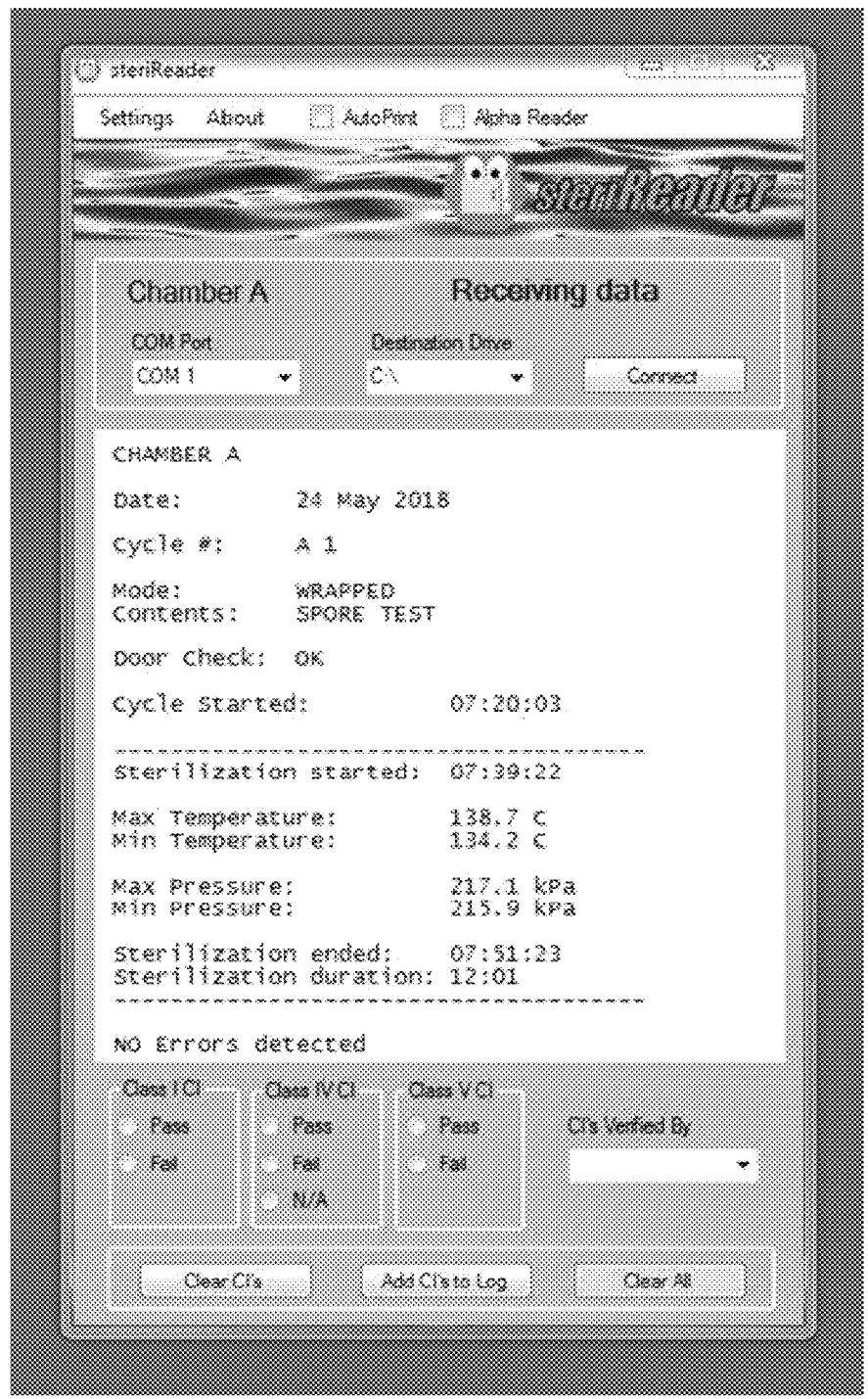
FIG. 6 is an example sterilization verification screen of the sterilization management application of the sterilization system of the present disclosure.

At operation 312, a staff member inspects the items in the load and verifies the mechanical indicators and chemical indicators. If the pouch or wrapping of an item is damaged, the item is rejected and is reprocessed (re-sterilized). The number of items sterilized in the load for which all of the chemical indicators matched predetermined criteria and which passed a visual inspection is input by the staff member into the sterilization management application 260 via its GUI (for example, at the end of the sterilization cycle). FIG. 6 is an example verification screen of the sterilization management application 260 for verification of the mechanical indicators and chemical indicators by a staff member.

At operation 314, the results of the sterilization cycle are stored in the sterilization database 165. Alternatively, data may be stored throughout the method 300 with the corresponding record being appended with new data as it is obtained. The sterilization database 165 includes daily and historical sterilization records for sterilization cycles performed for the medical or dental practice. For each sterilization cycle, the following information is stored in a corresponding record in the sterilization database 165:

date of sterilization;
sterilizer name (i.e., the unit which sterilized the item);
load number;
load type (or item type);
the number of items sterilized in the load for which all of the chemical indicators matched predetermined criteria and which passed a visual inspection;
mechanical indicator status/values;
chemical indicator status/values such as Class 1 chemical indicator pass/fail, Class 4 chemical indicator pass/fail/ N/A and Class 5 chemical indicator pass/fail;
staff member who inspected and verified the mechanical indicators and optionally recorded the mechanical indicators (if not reported directly by the sterilizer);
staff member who inspected and verified the chemical indicators as being passed; and
staff member who inspected and verified the integrity of the pouch or wrapping containing the sterilized item(s) (if any).

As noted above, the staff member is identified by an identifier (ID), which may be a proper name, initials, employee number or other suitable identifier that uniquely identifies the staff member. The staff member performing each of the above-noted tasks for a given sterilization cycle may be the same or vary, depending on the medical or dental practice and/or staffing. When the staff member perform the above-noted tasks is the same, a single staff member ID may be provided.

At operation 316, a sterilization label is generated based on the sterilization data for the item by the controller 110 and/or sterilized item labeller 160, printed by the sterilized item labeller 160, and applied to each sterilized item. The sterilization label may be generated automatically in response to a trigger condition, such as verification of the mechanical indicators and chemical indicators by the staff member or possibly a determination that MI values and CI statues match predetermined criteria. As noted above, the sterilization label specifies at least the date of sterilization, sterilizer name, load number and/or cycle number, number of items sterilized in the load for which all of the chemical indicators matched predetermined criteria and which passed a visual inspection, and the staff member who inspected the mechanical indicators and chemical indicators, and the integrity of the pouch or wrapping containing the sterilized item(s). Also as noted above, the sterilized item labeller 160 may print the sterilization label for the most recent successful sterilization cycle in response to detection of a sterilized item or other object by a sensor coupled to the sterilized item labeller 160.

At operation 318, the sterilized items are placed in quarantine.

At operation 320, a biological indicator test is performed.

At operation 322, it is determined whether the biological indicator test passed or failed. If the biological indicator test failed, the sterilization cycle failed and must be repeated, with operations returning to 302. When the sterilization cycle fails, each item in the load is considered non-sterile and must be re-sterilized. If the biological indicator test passed, the sterilization cycle was successful and operations proceed to operation 324. At operation 324, the sterilized items are released from quarantine because the BI test passed, the sterilization cycle was successful and the quarantine period has expired. The duration of the quarantine period corresponds to the duration of the biological indicator test which may be, for example, 24 minutes to 180 minutes.

It will be appreciated that the operations 318-324 are optional and are only performed when a biological indicator is included in the sterilization cycle.

Figure 3B:
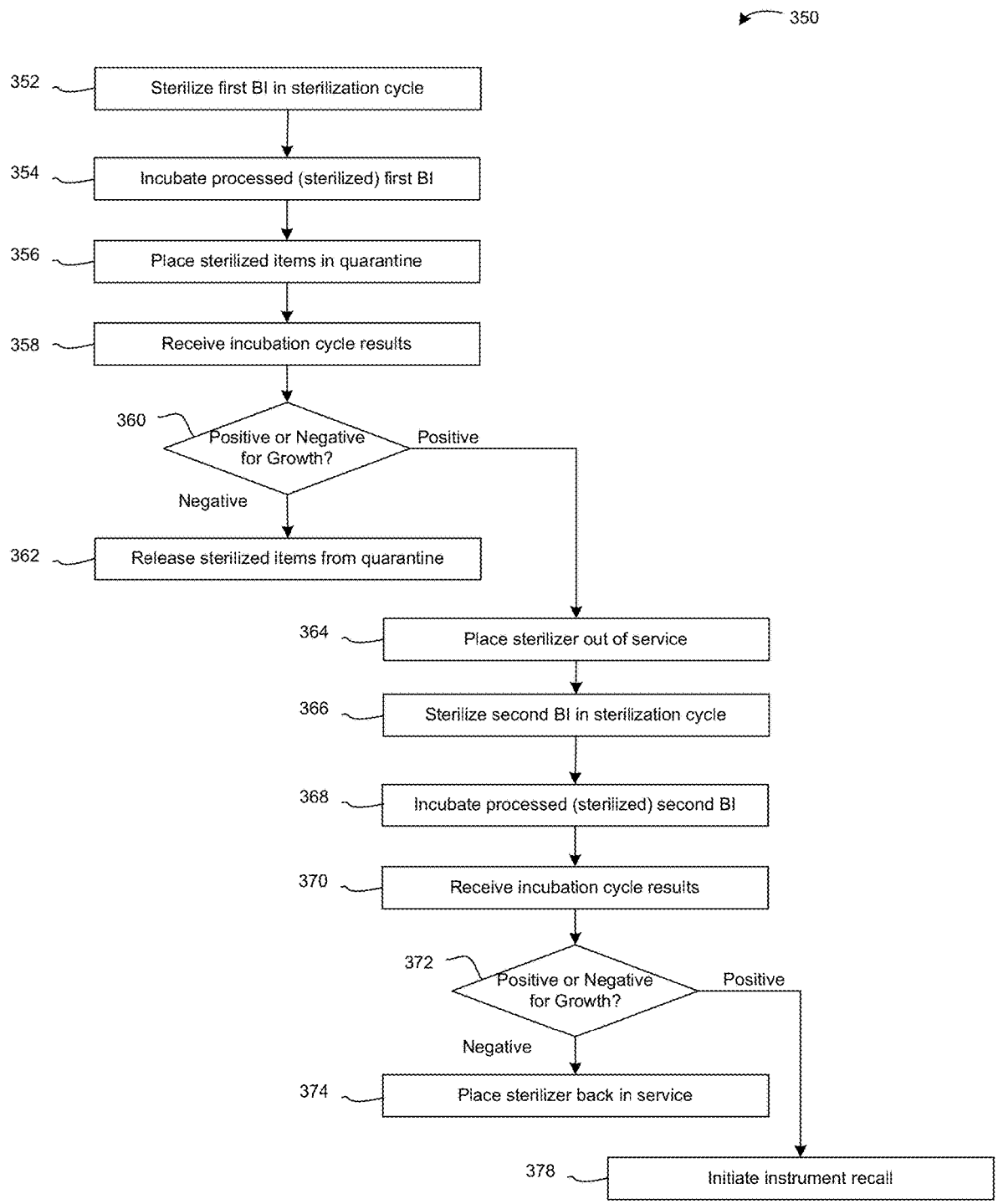
FIG. 3B is a flowchart illustrating a method of performing a biological indicator test in accordance with one example embodiment of the present disclosure.

Referring next to FIG. 3B, a method 350 of performing a biological indicator test in accordance with one example embodiment of the present disclosure will be described. The method 350 may be used to perform the operations 318-324 of method 300. At operation 352, a first biological indicator (BI) is processed (sterilized) in a sterilization cycle of a sterilizer 120. At operation 354, the processed (sterilized) first BI is incubated in an incubation cycle of an incubator 130. One or more processed BIs and optionally an unprocessed BI (BI control) may be incubated in the incubation cycle of the incubator 130. At operation 356, any items sterilized with the first BI are quarantined until the end of the incubation cycle of the incubator 130. The sterilized items are placed in quarantine for the duration of the biological indicator test which may be, for example, 24 minutes to 180 minutes. At operation 358, the incubation cycle results of the incubation cycle of the incubator 130 are output to, and received by, the controller 110. The controller 110 receives the data output by the incubator 130, and displays the results in the GUI of the sterilization management application 260. In some embodiments, the incubation cycle result specifies, for each well in which a biological indicator was present, a biological indicator pass/fall (i.e., BI result), a well ID, a time of biological indicator pass/fail, and a time when quarantine expired.

At operation 360, it is determined whether or not growth was detected by the incubator 130 in the processed first BI. As described above, a negative result from the incubator 130 for a processed BI indicates that growth of the spores in the processed BI was not detected by the incubator 130 and a successful sterilization process. The output of a negative result will only be generated by the incubator 130 after the end of the incubation cycle, and is output to the controller 110. A positive result from the incubator 130 for a processed BI indicates that growth of the spores in the processed BI was detected by the incubator 130 and a failure in the sterilization process. The output of a positive result will typically be generated by the incubator 130 in real-time or near real-time, i.e. immediately after the spore growth and/or sterilization cycle failure is detected, and is output to the controller 110.

If growth is not detected (a negative result), the sterilization cycle was successful and operations proceed to 362 at which any items sterilized in quarantine are released. If growth is detected (a positive result), the sterilization cycle has failed and operations proceed to 364 at which the sterilizer 120 in which the first BI was processed/sterilized is placed out of service. At operation 366, a second biological indicator (BI) is processed (sterilized) in a sterilization cycle of the sterilizer 120. Typically, the second BI is the only item in the sterilizer 120 for the second sterilization cycle but instruments may be included if desired. At operation 368, the processed (sterilized) second BI is incubated in an incubation cycle of an incubator 130 One or more processed BIs and optionally an unprocessed BI (BI control) may be incubated in the incubation cycle of the incubator 130. At operation 370, the incubation cycle results of the incubation cycle of the incubator 130 are output to, and received by, the controller 110.

At operation 372, it is determined whether or not growth was detected by the incubator 130 in the processed first BI. If growth is not detected (a negative result), the sterilization cycle was successful and operations proceed to 374 at which the sterilizer 120 is placed back in service. If growth is detected (a positive result), the sterilization cycle has failed a second time and operations proceed to 378 at which an instrument recall is initiated.

Figure 3C:
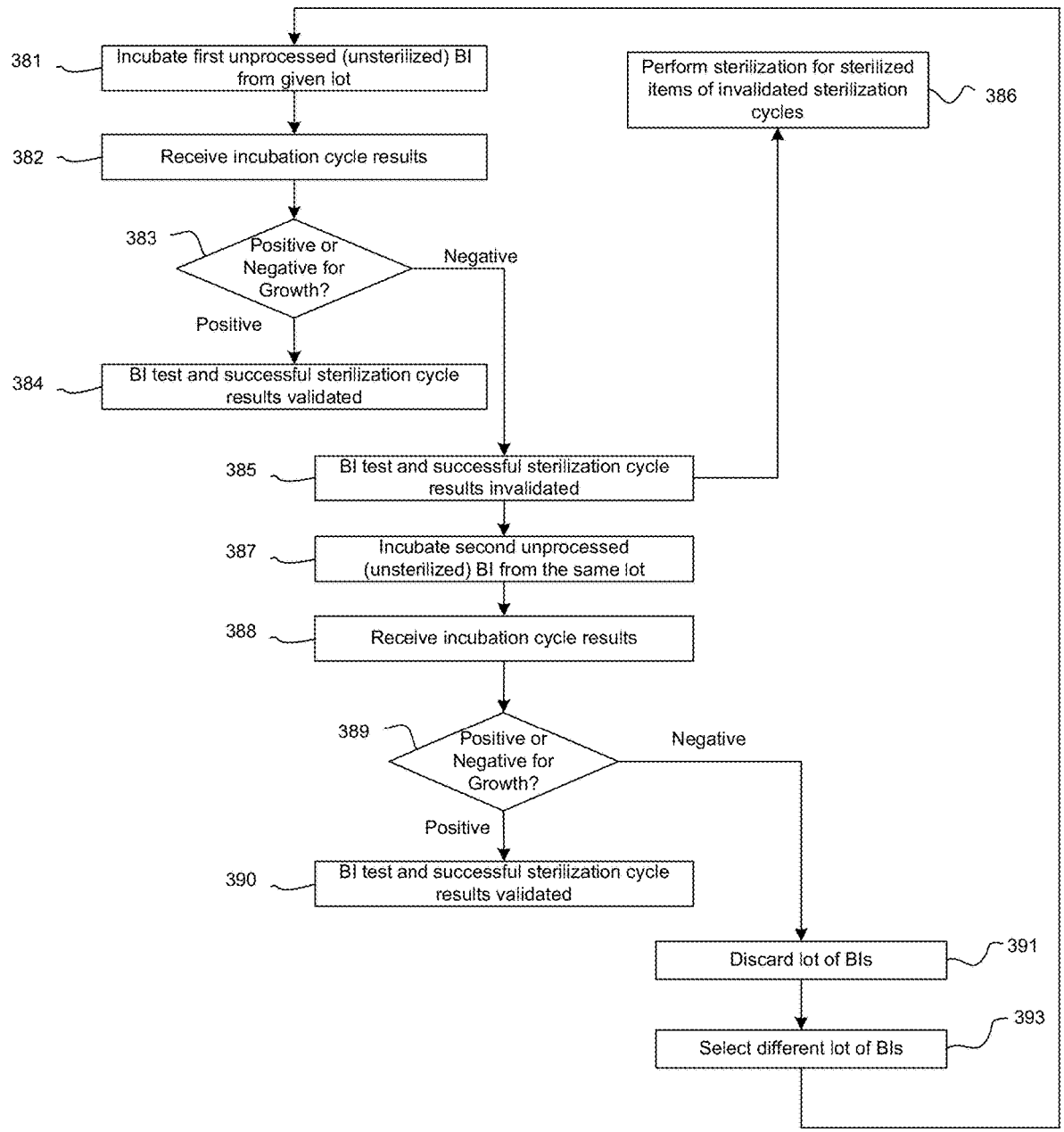
FIG. 3C is a flowchart illustrating a method of performing a biological indicator control test in accordance with one example embodiment of the present disclosure.

Referring next to FIG. 3C, a method 380 of performing a biological indicator control test in accordance with one example embodiment of the present disclosure will be described. A daily control is required for each lot from which a BI was used that day. At operation 381, a first unprocessed (unsterilized) BI is incubated in an incubation cycle of an incubator 130. The first unprocessed BI (BI control) may be incubated in the incubation cycle of the incubator 130 along with one or more processed BIs. At operation 382, the incubation cycle results of the incubation cycle of the incubator 130 are output to, and received by, the controller 110.

At operation 383, it is determined whether or not growth was detected by the incubator 130 in the first unprocessed BI. As described above, a negative result from the incubator 130 for an unprocessed BI indicates that growth of the spores in the processed BI was not detected by the incubator 130 and a BI control test failure. The output of a negative result will only be generated by the incubator 130 after the end of the incubation cycle, and is output to the controller 110. A positive result from the incubator 130 for an unprocessed BI indicates that growth of the spores in the processed BI was detected by the incubator 130 and a successful BI control test. The output of a positive result will typically be generated by the incubator 130 in real-time or near real-time, i.e. immediately after the spore growth and/or sterilization cycle failure is detected, and is output to the controller 110.

If growth is detected (a positive result), the BI control test is successful, and operations proceed to 384 at which all BI tests for BIs from the same lot on the same day and all successful sterilization cycle results for the same day are validated. If growth is not detected (a negative result), the BI control test failed, and operations proceed to 385 at which all BI tests for BIs from the same lot on the same day and all successful sterilization cycle results for the same day are invalidated At operation 387, a second unprocessed (unsterilized) BI is incubated in an incubation cycle of an incubator 130. The second unprocessed BI (BI control) may be incubated in the incubation cycle of the incubator 130 along with one or more processed BIs. At operation 388, the incubation cycle results of the incubation cycle of the incubator 130 are output to, and received by, the controller 110. At operation 389, it is determined whether or not growth was detected by the incubator 130 in the first unprocessed BI. If growth is detected (a positive result), the BI control test is successful, and operations proceed to 390 at which all BI tests for BIs from the same lot on the same day and all successful sterilization cycle results for the same day are validated. If growth is not detected (a second negative result), the BI control test failed, and operations proceed to 391 at which the lot of BIs is safely discarded.

At operation 393, a different lot of BIs is selected and operations return to 381. The method 380 is repeated until a positive BI control test is obtained. Once a positive BI control test is obtained, a new BI test is performed for each sterilizer 120. Items from all invalidated sterilization cycles are then re-sterilized. One or more items may be included in the sterilization cycle for the sterilizers 120.

It will be appreciated that the methods 350 and 380 relate to biological indicators and biological indicator controls, are not necessarily performed in each sterilization cycle. For example, a biological indicator is typically included in the first sterilization cycle of the day, the first sterilization cycle after a failed or invalidated sterilization cycle, or if required by the public health regulations for the load type.

Although not shown in FIG. 3A-3C, the controller 110 typically displays on the display 232 the results of the various operations and data received from the various devices, such as the output of the sterilizer 120, the incubator 130, scanner 140, and personnel identifier 150, and the results of the mechanical indicators, chemical indicators, and biological indicators of a load. Also, at the start of the method, or at one or more times during the method, the identity of the staff member using the sterilization management application 260, i.e. confirming the mechanical indicators, chemical indicators, and biological indicators, may be detected by the personnel identifier 150 or input by the staff member, for example, via a drop-down box in the GUI of the sterilization management application 260.

Figure 4:
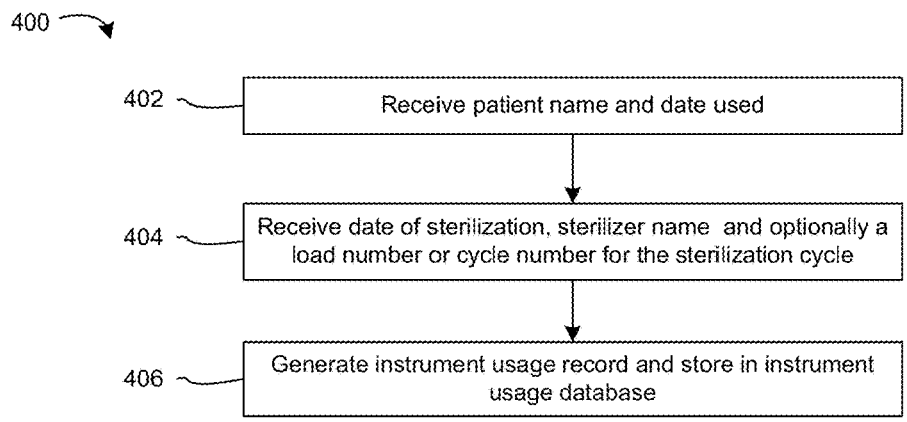
FIG. 4 is a flowchart illustrating a method of updating an instrument usage database when a sterilized item is used during a procedure in accordance with one example embodiment of the present disclosure.

Referring next to FIG. 4, a method 400 of updating the instrument usage database 170 when a sterilized item is used during a procedure in accordance with one embodiment of the present disclosure will be described. At least some of the method 300 may be performed by the controller 110, for example, via the processor 202. The operations may be performed in a differing order, or operations may be added, deleted, or modified in other embodiments.

At operation 402, a patient name and date used are provided to the controller 110. This may be provided by a GUI of the sterilization management application 260 via corresponding text entry fields. The patient name field may be a drop-down (or pull-down) box that allows a user to select a patient name from the patient database 180. The date used may use the current date provided by a real-time clock of the controller 110 or a drop-down box that allows a user to select a date.

At operation 404, a QR code on the sterilization label of an item to be used (e.g., pouch, cassette or special item) is scanned by the scanner 140 or a separate bar code scanner, depending on the embodiment. The QR code is read by the scanner 140 and the output is sent to and received by the controller 110 which searches for and extracts data from a corresponding sterilization record in the sterilization database 165 using the data from the QR code, namely the date of sterilization, sterilizer name (i.e., the unit which sterilized the item) and optionally a load number or cycle number for the sterilization cycle in which the item was sterilized. The sterilization data may be displayed on the display 232 of the controller 110. Alternatively, the date of sterilization, a sterilizer name and a load number for the sterilization cycle in which the item was sterilized may be input manually by a staff member.

At operation 406, an instrument usage record is generated and stored in the instrument usage database 170. As noted above, in some embodiments each record in the instrument usage database 170 may comprise a record ID, patient name, date of use, date of item sterilization, sterilizer ID, load number or cycle number, load type (or item type), and the number of items sterilized in the load for which all of the chemical indicators matched predetermined criteria and which passed a visual inspection.

Figure 5:
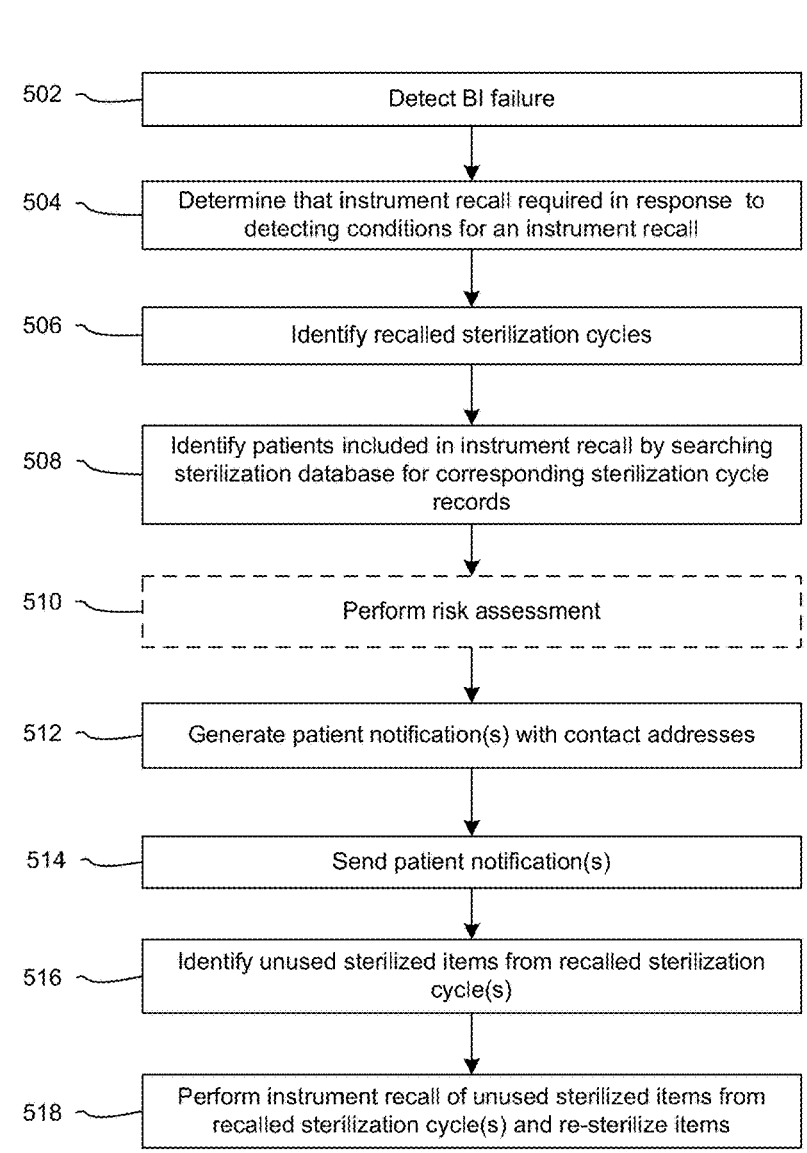
FIG. 5 is a flowchart illustrating a method of performing an instrument recall using the sterilization system of the present disclosure in accordance with one example embodiment of the present disclosure.

Referring next to FIG. 5, a method 500 of performing an instrument recall using the sterilization system in accordance with one embodiment of the present disclosure will be described. At least some of the method 300 may be performed by the controller 110, for example, via the processor 202. The operations may be performed in a differing order, or operations may be added, deleted, or modified in other embodiments.

At operation 502, a BI failure is detected for a sterilizer 120, i.e. a positive growth result is detected for a well of the incubator 130 corresponding to the sterilizer 120. The BI failure is detected by the incubator 130 and output to the controller 110, which automatically detects the BI failure.

At operation 504, the controller 110 determines that an instrument recall is required in response to detecting conditions for an instrument recall, such as a first or second BI test failure for a particular sterilizer 120. The detection of a BI test failure for a particular sterilizer 120 may be based on data or input received by the controller 110. Alternatively, the requirement for an instrument recall may be determined manually.

At operation 506, the controller 110 identifies sterilization cycles to be recalled based on the failed sterilization cycle of the sterilizer 120. This comprises identifying all sterilization cycles performed by the sterilizer 120 since the last successful BI test was obtained for the sterilizer 120, i.e. last negative BI result was obtained for the sterilizer 120. Typically, this will be the sterilization cycles from the last date on which the sterilizer 120 was used. These sterilization cycles are to be recalled and the items contained in the recalled sterilization cycles are considered non-sterile and must be re-sterilized. In some embodiments, the controller 110 is configured to determine a failed sterilization cycle of a sterilizer in response to failure of a biological indicator test for the sterilizer, and identify sterilization cycles to be recalled based on the failed sterilization cycle. The controller 110 may performed these operations automatically, without user intervention. In some embodiments, the controller 110 is configured to identify sterilization cycles to be recalled based on the failed sterilization cycle by identifying sterilization cycles performed via the sterilizer since a last successful biological indicator test was obtained for the sterilizer.

At operation 508, the instrument usage database 170 is searched to identify one or more patients for whom an item in a recalled sterilization cycle was used based on a sterilizer ID and a sterilization date for the recalled sterilization cycle. In environments in which a single sterilizer is used, a default value for the sterilizer ID may be used or the sterilizer ID may be omitted from the search parameters. The sterilization cycle parameters (i.e., sterilizer ID and sterilization date) for the recalled sterilization cycle may be received by the controller 110 automatically in response to the output from the incubator 130 (i.e., BI failure) or the controller 110 determination that an instrument recall is required. Alternatively, the sterilization cycle parameters for the recalled sterilization cycle may be input manually by a staff member.

At operation 510, a risk assessment is performed to determine whether the one or more patients for whom an item in the recalled sterilization cycle was used should be notified. The risk assessment may be automated based on patient information in the patient database 180. The patient information used in the risk assessment comprises individual patient information and demographics for the patient population of the medical or dental practice and its geography. Other patient information may be used in the risk assessment in other embodiment, the factors being considered may vary according to public health regulations. When the assessed risk is greater than or equal to a risk threshold, patients are notified. When the assessed risk is less than the risk threshold, patients are not notified.

The operation 510 is optional and may be omitted in some embodiments. For example, a risk assessment may be performed in advance (the risk may be predetermined) for individual patients and a decision regarding whether to notify individual patients may be made in advance (predetermined) for patients in the patient database 180. Thus, if one or more patients are included in an instrument recall and the decision regarding whether to notify at least some of those patients has been predetermined, the notification procedure is greatly simplified for some or all of the affected patients. In instances in which the decision whether to a notify patient has been predetermined for all patients affected by the instrument recall, the notification may be automatically generated and sent by the controller 110 without user intervention, thereby allowing patients to be automatically notified. In other examples, a decision to always notify patients included in an instrument recall may be made in advance (predetermined).

At operation 512, in response to determining that one or more patients for whom an item in the recalled sterilization cycle was used should be notified about the recalled sterilization cycle, a patient notification is generated. The patients may be notified automatically by the controller 110 or a coupled system in some embodiments. For example, the patients may be notified by telephone using an automated call distributor (ACD) which calls patients at a telephone number extracted from the patient database 180 based on the patient names and plays a generated voice message, for example based on text-to-speech synthesis, or an automated messaging application which generates and sends an electronic message to patients at a contact address extracted from the patient database 180 based on the patient names. Alternatively, the patients may be notified by a staff member.

The embodiment of FIG. 5 uses an automated messaging application. At operation 512, the controller 110 generates an electronic message about the recalled sterilization cycle for each patient for whom an item in the recalled sterilization cycle was used. The electronic message is typically an email message but may be a text message or instant message. The electronic message includes information about the recalled sterilization cycle and patient instructions. The patient instructions may include information or recommendations based on individual patient information and demographics for the patient population from the patient database 180, among other factors. For example, if a patient included in the instrument recall has a communicable disease or the patient population has a rate of a communicable disease, the patient instructions may include a recommendation for medical testing concerning the communicable disease(s). The controller 110 automatically populates each electronic message with a contact address for the respective patient. The contact address for each electronic message is determined from the patient database 180 using the patient name. At operation 514, the controller 110 sends each electronic message to the respective contact address.

At operation 516, the controller 110 identifies unused items from the recalled sterilization cycle by searching the instrument usage database 170 based on the sterilization cycle parameters for the recalled sterilization cycle, i.e., sterilizer ID and sterilization date. At operation 518, an instrument recall for the identified unused items from the recalled sterilization cycle is performed (e.g., the recall instruments are retrieved from storage) and a new sterilization cycle is performed on the recalled items from the recalled sterilization cycle.

FIG. 18 is a flowchart illustrating a method 600 of performing an instrument sterilization and recall in accordance with one example embodiment of the present disclosure. At least some of the method 600 may be performed at least partially by the controller 110, for example, by the processor 202, or other computing device. The operations may be performed in a differing order, or operations may be added, deleted, or modified in other embodiments.

At operation 602, the processor 205 receives from the sterilizer 120 first sterilization cycle data for a sterilization cycle, the first sterilization cycle data comprising one or more mechanical indicator values for a sterilization cycle. The first sterilization cycle data may further comprise a date of sterilization identifying a date upon which a sterilization cycle was performed, a sterilizer ID identifying a sterilizer used in the sterilization cycle, a load type, and a load number and/or a cycle number. Alternatively, the processor 205 may receive some or all of the first sterilization cycle data via input, for example, when the sterilizer 120 is not capable of, or configured to, output sterilization cycle data to the controller 110.

At operation 604, the processor 205 receives second sterilization cycle data for the sterilization cycle. The second sterilization cycle data comprises chemical indicator values, a number of items sterilized in the load for which all of the chemical indicators matched predetermined criteria and which passed a visual inspection, an ID of a staff member who inspected and verified the mechanical indicators, an ID of a staff member who inspected and verified the chemical indicators as being passed, and an ID of a staff member who inspected and verified the integrity of the pouch or wrapping containing the respective item. As noted above, the staff member ID may be a proper name, initials, employee number or other suitable identifier that uniquely identifies the staff member. The ID of the staff member may be the same in some working environments. The second sterilization cycle data may be partially or completely input by a user such as a staff member depending on the configuration of the system 100. The ID of the staff member using the sterilization management application 260, i.e. confirming the mechanical indicators, chemical indicators and/or biological indicators, may be detected by the personnel identifier 150 or input by the staff member, for example, via a drop-down box in the GUI of the sterilization management application 260.

At operation 608, the processor 205 determines whether the mechanical indicators and chemical indicator values for the sterilization cycle match predetermined criteria.

At operation 610, in response to a determination that mechanical indicators and chemical indicator values for the sterilization cycle match predetermined criteria, the processor 205 automatically generates a sterilization record in accordance with the first sterilization cycle data and second sterilization cycle data. The determination is made by the processor 205. The determination may be based on input and/or data for the mechanical indicators and chemical indicators received by the controller 110. In some examples, the determination made by the processor 205 is verified by a staff member. The staff member verification may be recorded by receiving corresponding input via the GUI of the sterilization management application 260, which stores the input verifying the result/determination in the sterilization record. The staff member may be identified by the personnel identifier 150, login status on the controller 110 or selection via the GUI of the sterilization management application 260, for example via a selection box of a data entry screen.

The sterilization record may comprise a number of fields. As noted above, the fields may comprise a date of sterilization identifying a date upon which a sterilization cycle was performed, a sterilizer ID identifying a sterilizer used in the sterilization cycle, a number of items sterilized in the load for which all of the chemical indicators matched predetermined criteria and which passed a visual inspection, the ID of a staff member who inspected and verified the mechanical indicators, the ID of a staff member who inspected and verified the chemical indicators as being passed, and the ID of a staff member who inspected and verified the integrity of the pouch or wrapping containing the respective item.

The sterilization record may further comprise mechanical indicator status/values and chemical indicator status. The mechanical indicator status/values may comprise a minimum and maximum temperature within the sterilizer during the sterilization cycle, a minimum and maximum pressure within the sterilizer during the sterilization cycle, and the duration of the sterilization cycle. The chemical indicator status may comprise a Class 1 chemical indicator pass/fail, Class 4 chemical indicator pass/fail/N/A and Class 5 chemical indicator pass/fail. The sterilization record may further comprise one or more of a load number and/or cycle number, a load type (or item type), and a number of items sterilized in the load for which all of the chemical indicators matched predetermined criteria and which passed a visual inspection.

At operation 612, the processor 205 automatically stores the sterilization record in the sterilization database 165 in the memory 226. A daily report may be generated for each sterilizer 120 of the sterilization cycle results for the sterilization cycles performed that day.

At operation 614, the processor 205 causes a printer (e.g., the labeller 160) to automatically prints one or more sterilization labels having printed thereon information for the sterilization cycle. Examples of the printed information on the label are described above, which may comprise a QR code. The processor 205 automatically determines the number of labels to print based on the number of items sterilized in the load for which all of the chemical indicators matched predetermined criteria and which passed a visual inspection in the sterilization record.

At operation 616, the processor 205 is configured to, in response to completion of an incubation cycle for a biological indicator, store the results of the incubation cycle in a corresponding record, for example, in a biological indicator test database (not shown). Each record comprises an incubation cycle result. In some embodiments, the incubation cycle result specifies, for each well in which a biological indicator was present, a biological indicator pass/fail, a well ID, a time of biological indicator pass/fail, and a time when quarantine expired. A daily report may be generated for each incubator 130 of the incubation cycle results for the incubation cycles performed that day. The daily incubation cycle report may be merged with the daily sterilization cycle report. If the biological indicator passed, the sterilization cycle has been successful. If the biological indicator failed, the sterilization cycle has failed and an instrument recall may be required.

At operation 618, after it is determined that an instrument recall is required, the processor 205 receives a patient name identifying a patient for whom an item in a recalled sterilization cycle was used, a date of use identifying a date upon which the item in the sterilization cycle was used, a sterilizer ID and a sterilization date. The determination of the instrument recall and the recalled sterilization cycles may be performed as set described above. The patient name and date of use are received in response to use of sterilized item in a procedure, for example, via input received via the GUI of the sterilization management application 260. The input may be provided manually via user input or automatically via scheduling software, depending on the instance. The sterilizer ID and sterilization date may be received via the scanner 140, the scanner 140 having extracted the sterilizer ID and sterilization date from a QR code located on a printed label attached to a pouch or wrapping in which the item was sterilized and kept. Alternatively, the controller 110 may extract the data from the QR code. Alternatively, a photo or scanner may be used to obtain a digital image of a sterilization label and the information may be extracted using optical character recognition and/or artificial intelligence/machine learning, depending on whether the sterilization label contains text only, a bar code or QR code only, or a combination thereof. Alternatively, the sterilization data may be extracted from the sterilization label via RFID reader (e.g., NFC reader) when the sterilization label includes an RFID tag.

At operation 620, the processor 205 automatically generates an instrument usage record in accordance with the received patient name and date of use, for example, in response to input. The instrument usage record comprising a number of fields. The fields may comprise a date of sterilization identifying a date upon which a sterilization cycle was performed, a sterilizer ID identifying a sterilizer used in the sterilization cycle, a patient name identifying a patient for whom an item in the sterilization cycle was used, and a date of use identifying a date upon which the item in the sterilization cycle was used. The fields may further comprise a load number identifying a load on the date of sterilization of the sterilization cycle and/or a cycle number identifying the sterilization cycle relative to a reference date, a number of items sterilized in the load for which all of the chemical indicators matched predetermined criteria and which passed a visual inspection.

At operation 622, the processor 205 automatically stores the instrument usage record in the instrument usage database in the memory 226.

At operation 624, the processor 205 performs an instrument recall routine for one or more recalled sterilization cycles in which the controller is configured to perform the operations 626, 628 and 630, described below. The instrument recall routine may be automatically triggered. For example, the processor 205 may receive, from the incubator 130, incubation cycle results for incubation cycles performed by the incubator 130, determine, from the incubation cycle results, whether each of the incubation cycles has passed or failed, and determine, from an incubation cycle result, that one or more sterilization cycles are to be recalled. This determination may be made in response to a determination that an incubation cycle for a processed biological indicator has failed, for example, based on an incubation well for which the incubation cycle result was obtained, and an identification of all sterilization cycles since the last successful BI test, i.e. last negative BI result, for the corresponding sterilizer 120. The controller 110 may be configured to automatically perform the instrument recall routine for the recalled sterilization cycle in response to the determination that the sterilization cycle is to be recalled At operation 626, the processor 205 identifies one or more patients for whom an item in the recalled sterilization cycle was used by comparing sterilization cycle parameters for the recalled sterilization cycle to a plurality of records of the instrument usage database 170. The sterilization cycle parameters may comprise a sterilizer ID and a sterilization date.

At operation 628, the processor 205 initiates a patient notification routine comprising at least one of outputting of identifying information of the one or more patients for whom an item in the recalled sterilization cycle was used and notifying the one or more patients for whom an item in the recalled sterilization cycle was used about the recalled sterilization cycle. The outputting may comprise displaying the matching patient information on a display of the controller 110.

In some examples, to notify the one or more patients for whom an item in the recalled sterilization cycle was used about the recalled sterilization cycle the controller is configured to: generate, by the processor 205, an electronic message about recalled sterilization cycle for each patient for whom an item in the recalled sterilization cycle was used; automatically populate, by the processor, each electronic message with a contact address for the respective patient, the contact address being determined from a patient database 180 using the patient name; and send, by via communication module 228 of the controller 110, each electronic message to the respective contact address. The electronic message includes information about the recalled sterilization cycle and patient instructions. The electronic message may be an email message.

At operation 630, the processor 205 identifies unused items from the recalled sterilization cycle by comparing sterilization cycle parameters for the recalled sterilization cycle to a plurality of records of the sterilization database 165 and optionally a plurality of records of the instrument usage database 170. For example, the unused items may be determined by the differences between the matching records in the sterilization database 165 and instrument usage database 170 (i.e., total sterilized items in the recalled sterilization cycle less items in the recalled sterilization cycle used on a patient determined in operation 626). Identifying information of the unused items may be output, for example, by displaying the identifying information of the unused items on a display of the controller 110. The unused items may be retrieved from storage by a staff member and re-sterilized. The unused items by the staff member by the recalled sterilization cycle may be identified by the corresponding sterilization labels printed thereon.

Example Graphical User Interface (GUI) Screens

Figure 7:
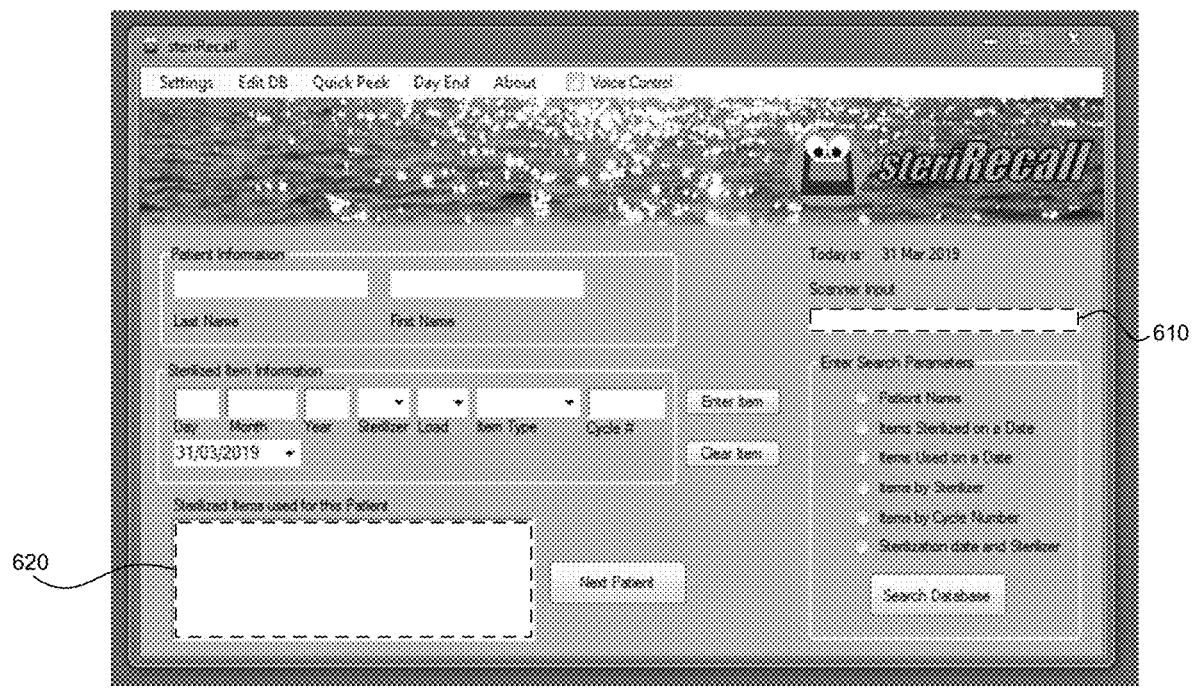
FIG. 7 is an example home screen of a recall function of the sterilization management application of the sterilization system of the present disclosure.

FIG. 7 is an example home screen of a recall function of the sterilization management application 260 of the sterilization system of the present disclosure. The home screen is the primary (or main) user interface screen. A patient name is entered by typing last name and first name into the designated text entry fields (or boxes). Information regarding a sterilized item for use with the patient may be entered manually in the entry boxes, which may be a drop-down style, or the item may be scanned with the scanner 140 or a separate barcode or QR scanner, which reads the QR code from the sterilization label. When the item information is input by scanning the QR code, the box 610 is populated with the encoded information from the QR code, which may in a space delimited format. The box 610 may be expandable or scrollable.

When valid item information is added, the information is immediately added to the instrument usage database 170. When the data has been successfully added to the database 170 by scanning a QR code or manually entering the date, an identifier for the item used for the patient is populated in box 620. The display of the identifier provides confirmation for the user that the item has been successfully scanned. An example identifier is 23 Jul. 2018 A 2 POUCH, indicating the date of sterilization as 23 Jul. 2018 A, the sterilizer ID as sterilizer "A", the load was the second load of the day, and the item is of type "POUCH". The sterilization management application 260 may be used to search the instrument usage database 170 using various parameters, which may be entered by the user. The sterilization management application 260 may be used to generate Recall Reports and to display, save and/or print Recall Reports. The reports may be saved to a designated location (e.g., database or folder) in a particular file format. The Recall reports may be saved, for example, to a dedicated Reports database or folder of the controller 110. The Reports database may be part of the instrument usage database 170. The Recall Report may be saved as text file or other suitable file format.

Figure 8:
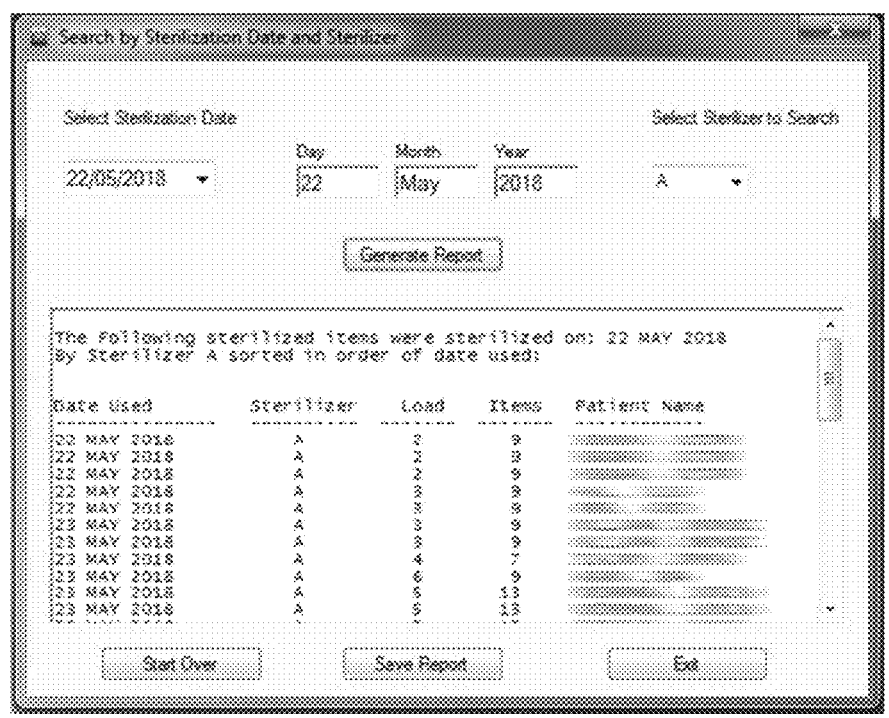
FIG. 8 is an example search screen of a recall function of the sterilization management application of the sterilization system of the present disclosure for searching by sterilization date and sterilizer.

FIG. 8 is an example search screen of the recall function of the sterilization management application 260 for searching by sterilization date and sterilizer. This is a multi-parameter search that can identify each item sterilized on a particular date and by a particular sterilizer, which may be selected by a drop-down menu, and which patients were treated with the sterilized items. The type of sterilized item (cassette, pouch or special) is identified. The items still in storage are also accounted for. An example Recall Report for Sterilizer A on 22 May 2018 is shown below:

The following sterilized items were sterilized on 22 May 2018 by Sterilizer A sorted in order of date used:

| Date Used | Sterilizer | Load | Items | Patient Name |
| --- | --- | --- | --- | --- |
| 22 MAY 2018 | A | 2 | 9 | VESPER SIENNA |
| 22 MAY 2018 | A | 2 | 9 | VESPER SIENNA |
| 22 MAY 2018 | A | 2 | 9 | VESPER SIENNA |
| 22 MAY 2018 | A | 3 | 9 | BRIDGET SOPHIE |
| 23 MAY 2018 | A | 3 | 9 | NAOMI PLUM |
| 23 MAY 2018 | A | 3 | 9 | NAOMI PLUM |
| 23 MAY 2018 | A | 3 | 9 | HEATHER BARRON |

The number of items still in storage to retrieve:

| Load | Items | Type |
| --- | --- | --- |
| 2 | 5 | SPECIAL |
| 3 | 1 | CASSETTE |
| 4 | 4 | CASSETTE |
| 5 | 2 | SPECIAL |
| 6 | 2 | CASSETTE |

Figures 9, 10:
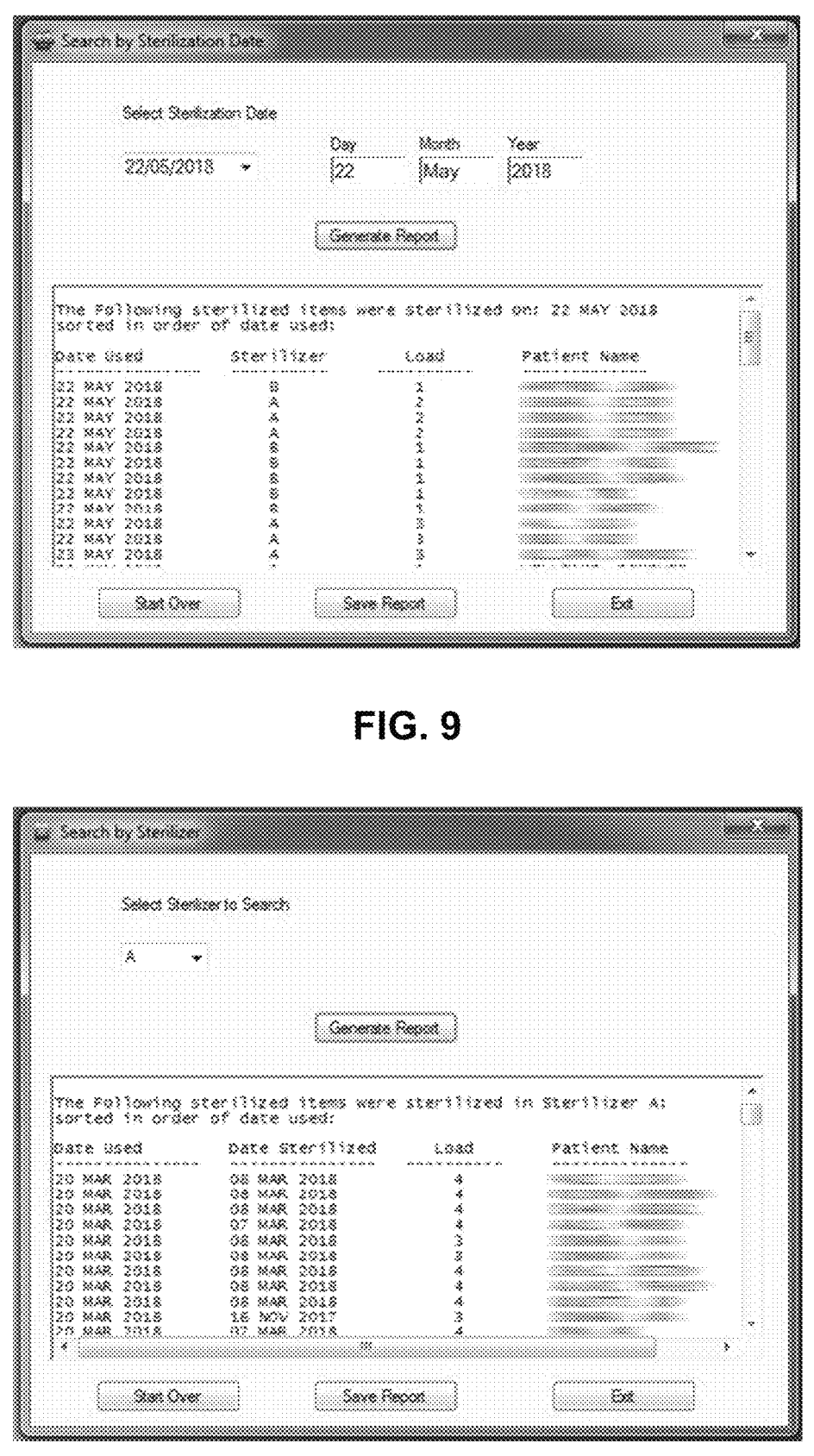

FIG. 9 is an example search screen of the recall function of the sterilization management application 260 for searching by sterilization date. Every item sterilized on a particular date, which may be selected by a drop-down menu, and the associated patients the items were used with can be identified since the first day of use of the sterilization management application 260. An example Recall Report for items that were sterilized items on 22 May 2018 is shown below:

The following sterilized items were sterilized on 22 May 2018 sorted in order of date used:

| Date Used | Sterilizer | Load | Patient Name |
| --- | --- | --- | --- |
| 22 MAY 2018 | B | 3 | VESPER SIENNA |
| 22 MAY 2018 | A | 3 | BRIDGET SOPHIE |
| 22 MAY 2018 | A | 3 | BRIDGET SOPHIE |
| 22 MAY 2018 | A | 2 | HEATHER BARRON |

-continued

| Date Used | Sterilizer | Load | Patient Name |
|---|---|---|---|
| 22 MAY 2018 | B | 3 | NAOMI PLUM |
| 23 MAY 2018 | A | 1 | ISABELLE SIMA |
| 23 MAY 2018 | B | 3 | ADDISYN RITA |

FIG. 10 is an example search screen of the recall function of the sterilization management application 260 for searching by sterilizer. Every item ever sterilized by a particular sterilizer, which may be selected by a drop-down menu, and the associated patients the items were used with can be identified since the first day of use of the sterilization management application 260. An example Recall Report for items that were sterilized by Sterilizer A as of 21 Mar. 2018 is shown below:

The following sterilized items were sterilized in Sterilizer A sorted in order of date used:

| Date Used | Date Sterilized | Load | Patient Name |
|---|---|---|---|
| 20 MAR. 2018 | 08 MAR. 2018 | 4 | VESPER SIENNA |
| 20 MAR. 2018 | 08 MAR. 2018 | 4 | BRIDGET SOPHIE |
| 20 MAR. 2018 | 07 MAR. 2018 | 4 | BRIDGET SOPHIE |
| 20 MAR. 2018 | 08 MAR. 2018 | 4 | HEATHER BARRON |
| 20 MAR. 2018 | 08 MAR. 2018 | 3 | NAOMI PLUM |
| 20 MAR. 2018 | 08 MAR. 2018 | 3 | ISABELLE SIMA |
| 20 MAR. 2018 | 07 MAR. 2018 | 4 | ADDISYN RITA |

Figures 11, 12:
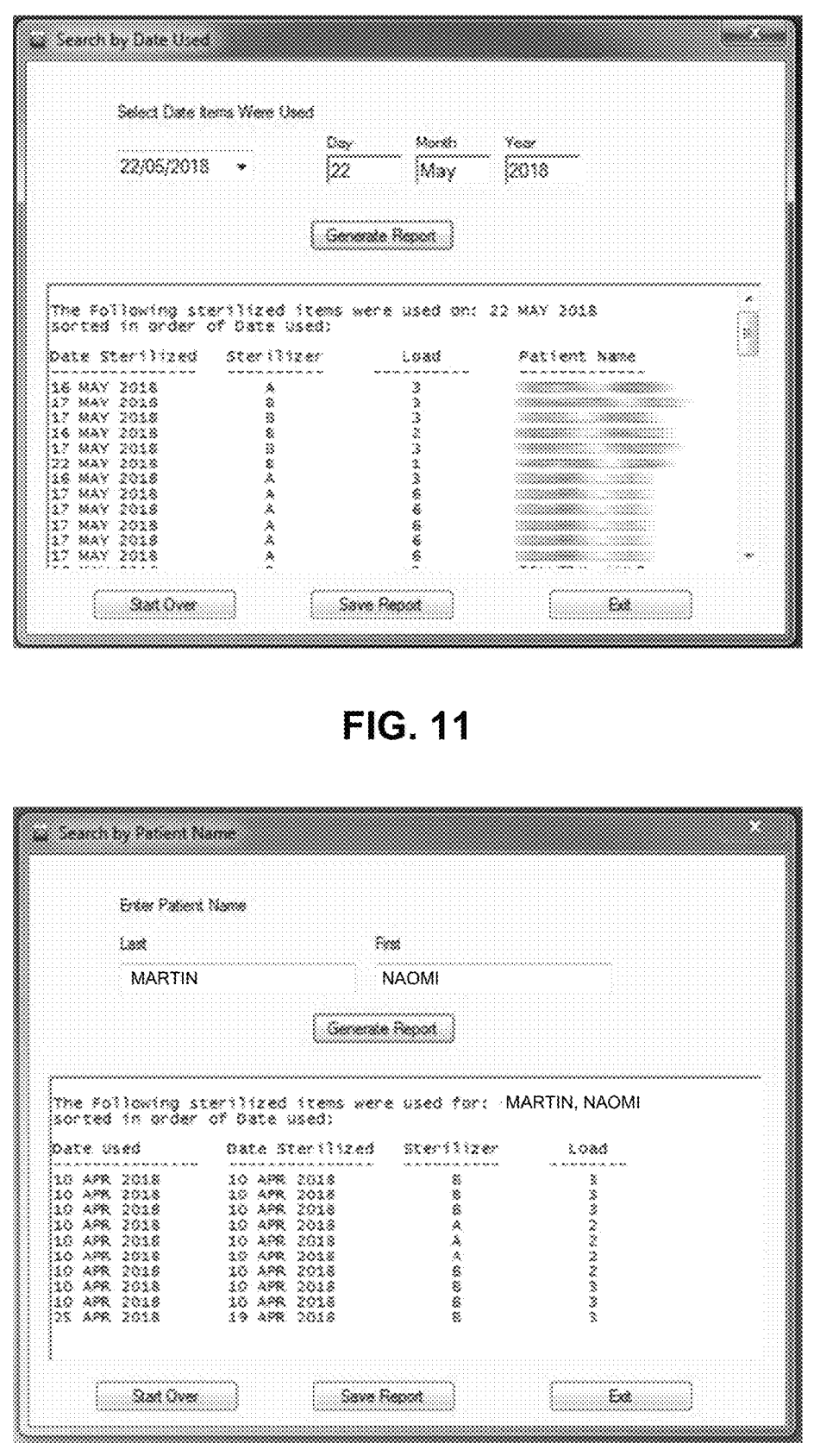

FIG. 11 is an example search screen of the GUI of the sterilization system of the present disclosure for searching by date used. Every item used on a particular date, which may be selected by a drop-down menu, and the associated patients the items were used with can be identified since the first day of use of the sterilization management application 260. An example Recall Report for sterilized items were used on 22 May 2018 is shown below:

The following sterilized items were used on 22 May 2018 sorted in order of date used:

| Date Sterilized | Sterilizer | Load | Patient Name |
|---|---|---|---|
| 16 MAY 2018 | A | 3 | VESPER SIENNA |
| 17 MAY 2018 | B | 3 | BRIDGET SOPHIE |
| 17 MAY 2018 | B | 3 | NAOMI PLUM |
| 16 MAY 2018 | B | 2 | HEATHER BARRON |
| 17 MAY 2018 | B | 3 | NAOMI PLUM |
| 22 MAY 2018 | B | 1 | ISABELLE SIMA |
| 16 MAY 2018 | A | 3 | ADDISYN RITA |

FIG. 12 is an example search screen of the recall function of the sterilization management application 260 of the present disclosure for searching by patient name. Every item ever used with each procedure can be identified since the first day of use of the sterilization management application 260. Patient last and first names are entered into the designated text entry fields (or boxes) of the screen. An example Recall Report for sterilized items were used for PLUM, NAOMI as of 22 May 2018 sorted in order of date used is shown below:

The following sterilized items were used for PLUM, NAOMI sorted in order of date used:

| Date Used | Date Sterilized | Sterilizer | Load |
|---|---|---|---|
| 10 APR. 2018 | 10 APR. 2018 | B | 3 |
| 10 APR. 2018 | 10 APR. 2018 | B | 3 |
| 10 APR. 2018 | 10 APR. 2018 | B | 3 |
| 10 APR. 2018 | 10 APR. 2018 | A | 2 |
| 10 APR. 2018 | 10 APR. 2018 | A | 2 |
| 10 APR. 2018 | 10 APR. 2018 | B | 3 |
| 25 APR. 2018 | 19 APR. 2018 | B | 3 |

Figure 13:
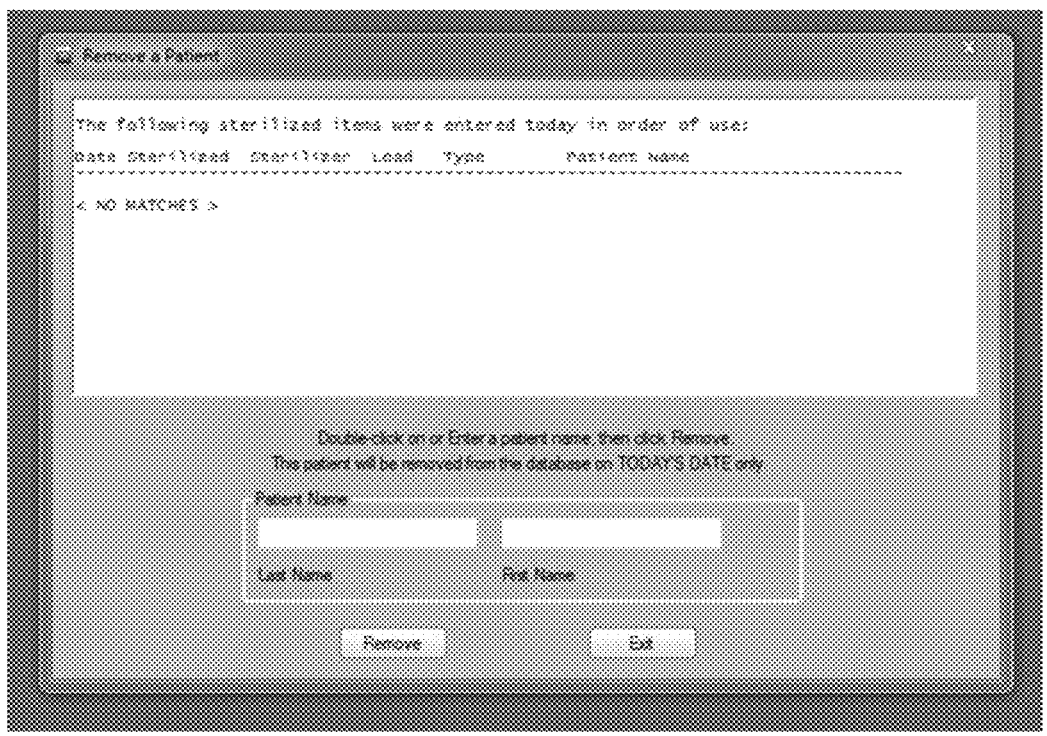
FIG. 13 is an example edit screen of the sterilization management application of the sterilization system of the present disclosure for removing data for a patient from the sterilization records.

FIG. 13 is an example of a first edit screen of the sterilization management application 260 of the sterilization system of the present disclosure for removing data for a patient from the sterilization records. The first edit screen allows a user to remove the entries for a particular patient on the present day only. This may be useful in cases in which items are scanned for use ahead of time but are not used, for example, because the procedure does not occur. The items are returned to storage and the information within the instrument usage database 170 is removed, preventing "false positive" associations of instrument and patient. The patient last and first names are entered into the designated text entry fields (or boxes) of the screen, and the sterilization management application 260 determines the current date from a real-time clock.

Figure 14:
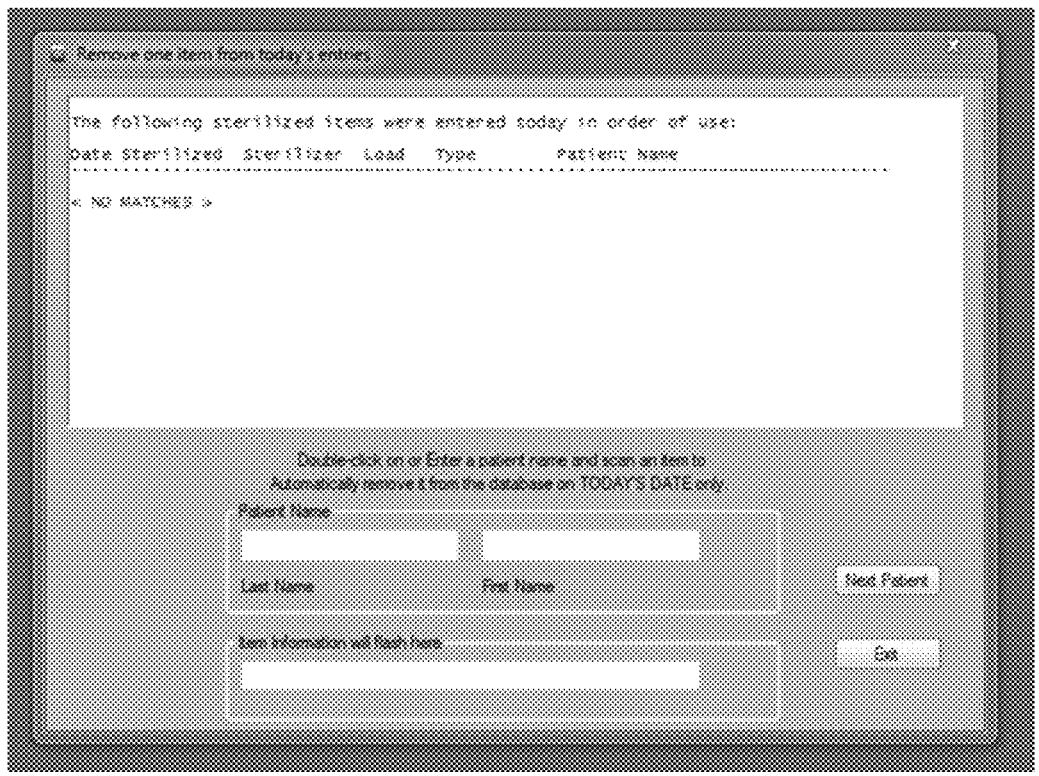
FIG. 14 is an example edit screen of the sterilization management application of the sterilization system of the present disclosure for removing data for a patient from the sterilization records based on a scanned Quick Response (QR) code.

FIG. 14 is an example of a second edit screen of the sterilization management application 260 of the sterilization system of the present disclosure for removing data for a patient from the sterilization records based on a scanned QR code. The second edit screen allows one item to be removed for a particular person on the present day only. This may be useful in cases in which an instrument is scanned for use ahead of time but is not being used for a procedure. It can be scanned and returned to storage and the information within the database is removed, preventing "false positive" associations of instrument and patient. The patient last and first names are automatically populated into the designated text entry fields (or boxes) of the screen in response to scanning the QR code on the corresponding instrument pouch, and the sterilization management application 260 determines the current date from a real-time clock.

Figure 15:
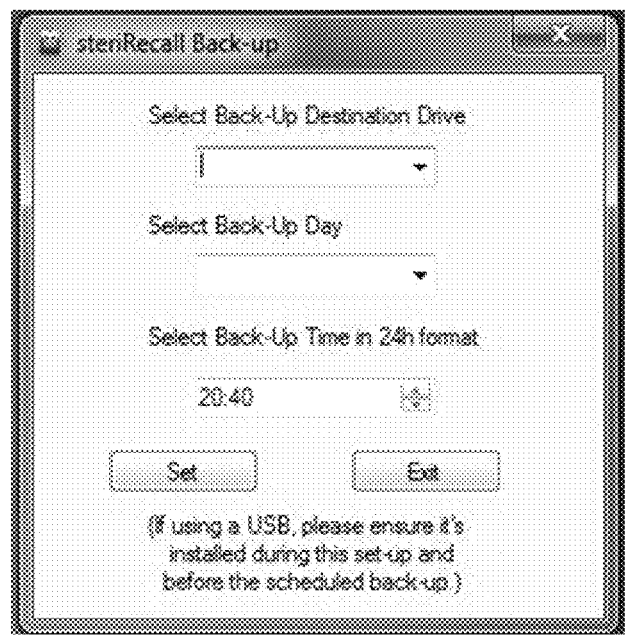
FIG. 15 is an example backup screen of a backup function of the sterilization management application of the sterilization system of the present disclosure for backup sterilization records.

FIG. 15 is an example backup screen of a backup function of the sterilization management application 260 of the sterilization system of the present disclosure for backup sterilization records. The backup function allows a user to schedule a backup of the instrument usage database 170 and to specify a location where the backup is saved.

Figure 17:
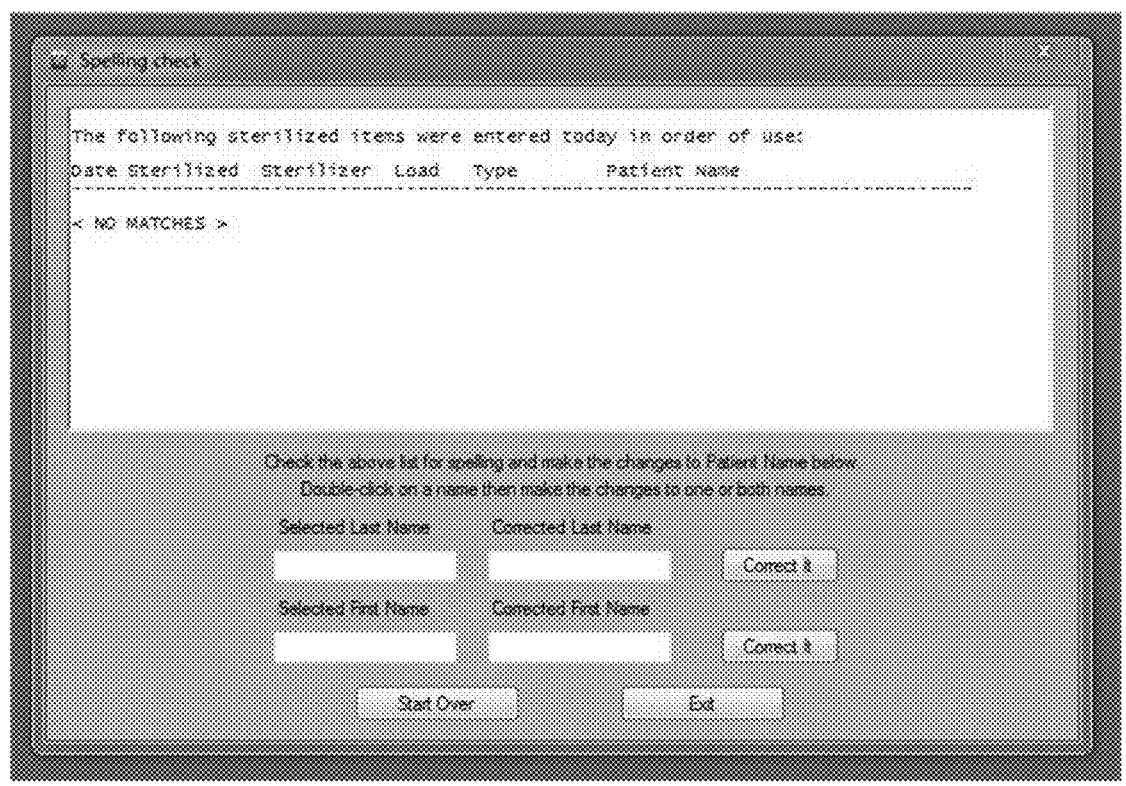
FIG. 17 is an example screen of a dialog for correcting a patient name in a record of the sterilization management application of the sterilization system of the present disclosure.

FIG. 17 is an example screen of a dialog for correcting a patient name in a record of the sterilization management application 260 of the sterilization system of the present disclosure. The dialog of FIG. 17 may be used to correct the name of a patient for whom a sterilized item is being used. For example, the dialog may be used to correct the patient name in an instrument usage record of the instrument usage database 170 from that extracted from a scanned QR code because the sterilized item or kit is being used with a different patient than originally intended.

General

The steps and/or operations in the flowcharts and drawings described herein are for purposes of example only. There may be many variations to these steps and/or operations without departing from the teachings of the present disclosure. For instance, the steps may be performed in a differing order, or steps may be added, deleted, or modified.

The coding of software for carrying out the above-described methods described is within the scope of a person of ordinary skill in the art having regard to the present disclosure. Machine readable code executable by one or more processors of one or more respective devices to perform the above-described method may be stored in a machine readable medium such as the memory of the data manager. The terms "software" and "firmware" are interchangeable within the present disclosure and comprise any computer program stored in memory for execution by a processor, comprising RAM memory, ROM memory, erasable programmable ROM (EPROM) memory, electrically EPROM (EEPROM) memory, and non-volatile RAM (NVRAM) memory. The above memory types are example only, and are thus not limiting as to the types of memory usable for storage of a computer program.

All values and sub-ranges within disclosed ranges are also disclosed. Also, although the systems, devices and processes disclosed and shown herein may comprise a specific plurality of elements/components, the systems, devices and assemblies may be modified to comprise additional or fewer of such elements/components. For example, although any of the elements/components disclosed may be referenced as being singular, the embodiments disclosed herein may be modified to comprise a plurality of such elements/components. The subject matter described herein intends to cover and embrace all suitable changes in technology.

Although the present disclosure is described, at least in part, in terms of methods, a person of ordinary skill in the art will understand that the present disclosure is also directed to the various components for performing at least some of the aspects and features of the described methods, be it by way of hardware (DSPs, ASIC, or FPGAs), software or a combination thereof. Accordingly, the technical solution of the present disclosure may be embodied in a non-volatile or non-transitory machine readable medium (e.g., optical disk, flash memory, etc.) having stored thereon executable instructions tangibly stored thereon that enable a processing device (e.g., a data manager) to execute examples of the methods disclosed herein.

The term "processor" may comprise any programmable system comprising systems using micro- or nano-processors/controllers, reduced instruction set circuits (RISC), application specific integrated circuits (ASICs), logic circuits, and any other circuit or processor capable of executing the functions described herein. The term "database" may refer to either a body of data, a relational database management system (RDBMS), or to both. As used herein, a database may comprise any collection of data comprising hierarchical databases, relational databases, flat file databases, object-relational databases, object oriented databases, and any other structured collection of records or data that is stored in a computer system. The above examples are example only, and thus are not intended to limit in any way the definition and/or meaning of the terms "processor" or "database".

The present disclosure may be embodied in other specific forms without departing from the subject matter of the clauses. The described example embodiments are to be considered in all respects as being only illustrative and not restrictive. The present disclosure intends to cover and embrace all suitable changes in technology. The scope of the present disclosure is, therefore, described by the included clauses rather than by the foregoing description. The scope of the clauses should not be limited by the embodiments set forth in the examples, but should be given the broadest interpretation consistent with the description as a whole.

The invention claimed is:

1. A sterilization system, comprising:
a controller comprising a processor and a memory coupled to the processor;
one or more sterilizers coupled to the controller;
a printer coupled to the controller;
wherein the controller is configured to:
receive, by the controller, first sterilization cycle data for the sterilization cycle, the first sterilization cycle data comprising one or more mechanical indicator values for the sterilization cycle;
receive, by the controller, second sterilization cycle data for the sterilization cycle; and
in response to a determination that mechanical indicators and chemical indicator values for the sterilization cycle match predetermined criteria,
automatically generate a sterilization record in accordance with the first sterilization cycle data and second sterilization cycle data,
automatically store, by the controller, the sterilization record in a sterilization database, the sterilization record comprising a number of fields, the fields comprising a date of sterilization identifying a date upon which a sterilization cycle was performed, a sterilizer identifier (ID) identifying a sterilizer used in the sterilization cycle, a load type, a number of items sterilized in the load for which all of the chemical indicators matched predetermined criteria and which passed a visual inspection, an ID of a staff member who inspected and verified the mechanical indicators, an ID of a staff member who inspected and verified the chemical indicators as being passed, and an ID of a staff member who inspected and verified the integrity of any pouch or wrapping containing the respective item, and
automatically cause, by the printer, printing of a sterilization label having printed thereon information for the sterilization cycle;
perform an instrument recall routine for a recalled sterilization cycle in dependence on sterilization cycle parameters for the recalled sterilization cycle in which the controller is configured to:
identify one or more patients for whom an item in the recalled sterilization cycle was used by comparing the sterilization cycle parameters for the recalled sterilization cycle to a plurality of records of an instrument usage database, each record of the instrument usage database comprising a number of fields, the fields comprising a date of sterilization identifying a date upon which a sterilization cycle was performed, a sterilizer ID identifying a sterilizer used in the sterilization cycle, a load ID identifying a load on the date of sterilization of the sterilization cycle, a number of items sterilized in the load for which all of the chemical indicators matched predetermined criteria and which passed a visual inspection, a patient name identifying a patient for whom an item in the sterilization cycle was used, and a date of use identifying a date upon which the item in the sterilization cycle was used; and
initiate a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

2. The sterilization system of claim 1, wherein the controller is configured to:
   determine a failed sterilization cycle of a sterilizer in response to failure of a biological indicator test for the sterilizer; and
   identify sterilization cycles to be recalled based on the failed sterilization cycle.

3. The sterilization system of claim 1, wherein the controller is configured to identify sterilization cycles to be recalled based on the failed sterilization cycle by identifying sterilization cycles performed via the sterilizer since a last successful biological indicator test was obtained for the sterilizer.

4. The sterilization system of claim 2, wherein the controller is configured to automatically, without user intervention, determine the failed sterilization cycle and identify sterilization cycles to be recalled.

5. The sterilization system of claim 1, wherein the controller is configured to, when performing the instrument recall routine for a recalled sterilization cycle:
   identify unused items from the recalled sterilization cycle by comparing sterilization cycle parameters for the recalled sterilization cycle to a plurality of records of the sterilization database.

6. The sterilization system of claim 1, wherein the sterilization cycle parameters for the recalled sterilization cycle comprise a sterilizer ID and a sterilization date.

7. The sterilization system of claim 1, wherein the determination that the mechanical indicators and chemical indicator values for the sterilization cycle match predetermined criteria is performed automatically by the controller in response to received data for the mechanical indicators and chemical indicators.

8. The sterilization system of claim 1, wherein the controller is configured to:
   receive data comprising one or more chemical indicators for the sterilization cycle;
   determine whether the mechanical indicators and chemical indicator values for the sterilization cycle match predetermined criteria.

9. The sterilization system of claim 1, further comprising:
   an incubator coupled to the controller;
   wherein the controller is configured to:
      receive, from the incubator, incubation cycle results for incubation cycles performed by the incubator;
      determine, from the incubation cycle results, whether an incubation cycles has passed or failed;
      determine, from an incubation cycle result, that a sterilization cycle has failed in response to a determination that an incubation cycle for a biological indicator has failed.

10. The sterilization system of claim 9, wherein the controller is configured to automatically perform the instrument recall routine for the recalled sterilization cycle in response to the determination that the sterilization cycle has failed.

11. The sterilization system of claim 1, wherein the controller is configured to:
   receive a patient name identifying a patient for whom a sterilized item was used and a date of use identifying a date upon which the sterilized item was used;
   receive a sterilizer ID and a sterilization date for the sterilization cycle in which the sterilized item was last sterilized;
   automatically generate an instrument usage record in accordance with the received patient name and date of use; and
   automatically store the instrument usage record in an instrument usage database, the instrument usage record comprising a number of fields, the fields comprising a date of sterilization identifying a date upon which a sterilization cycle was performed, a sterilizer identifier (ID) identifying a sterilizer used in the sterilization cycle, a load number identifying a load on the date of sterilization of the sterilization cycle and/or a cycle number identifying the sterilization cycle relative to a reference date, a number of items sterilized in the load for which all of the chemical indicators matched predetermined criteria and which passed a visual inspection, an item type, a patient name identifying a patient for whom an item in the sterilization cycle was used, and a date of use identifying a date upon which the item in the sterilization cycle was used.

12. The sterilization system of claim 11, wherein the sterilizer ID and sterilization date are received via a scanner coupled to the controller, the scanner having extracted the sterilizer ID and sterilization date from a QR code associated with the item.

13. The sterilization system of claim 1, wherein the controller is configured to notify the one or more patients for whom an item in the recalled sterilization cycle was used about the recalled sterilization cycle by:
   generating an electronic message about recalled sterilization cycle for each patient for whom an item in the recalled sterilization cycle was used;
   automatically populating each electronic message with a contact address for the respective patient, the contact address being determined from a patient database using the patient name; and
   sending, via communication module of the controller, each electronic message to the respective contact address.

14. The sterilization system of claim 13, wherein the electronic message includes information about the recalled sterilization cycle and patient instructions.

15. The sterilization system of claim 1, wherein the information printed on the label comprises a QR code.

16. The sterilization system of claim 1, wherein the sterilization record further comprises mechanical indicator status/values and chemical indicator status.

17. The sterilization system of claim 16, wherein the mechanical indicator status/values comprises a minimum and maximum temperature within the sterilizer during the sterilization cycle, a minimum and maximum pressure within the sterilizer during the sterilization cycle, and the duration of the sterilization cycle.

18. The sterilization system of claim 16, wherein the chemical indicator status comprises a Class 1 chemical indicator pass/fail, Class 4 chemical indicator pass/fail/N/A and Class 5 chemical indicator pass/fail.

19. The sterilization system of claim 1, wherein the sterilization record further comprises one or more of a load number and/or cycle number, a load type, and a number of items sterilized in the load for which all of the chemical indicators matched predetermined criteria and which passed a visual inspection.

20. A computer-implemented method of performing an instrument recall, wherein the method is performed by a controller comprising a processor and a memory coupled to the processor, the controller coupled to one or more sterilizers and a printer, the method comprising:

receiving first sterilization cycle data for the sterilization cycle, the first sterilization cycle data comprising one or more mechanical indicator values for the sterilization cycle;

receiving second sterilization cycle data for the sterilization cycle; and in response to a determination that mechanical indicators and chemical indicator values for the sterilization cycle match predetermined criteria, automatically generating a sterilization record in accordance with the first sterilization cycle data and second sterilization cycle data, automatically storing the sterilization record in a sterilization database, the sterilization record comprising a number of fields, the fields comprising a date of sterilization identifying a date upon which a sterilization cycle was performed, a sterilizer identifier (ID) identifying a sterilizer used in the sterilization cycle, a number of items for which all of the chemical indicators matched predetermined criteria and which passed a visual inspection, an ID of a staff member who inspected and verified the mechanical indicators, an ID of a staff member who inspected and verified the chemical indicators as being passed, and an ID of a staff member who inspected and verified the integrity of the pouch or wrapping containing the respective item, and automatically printing a sterilization label having printed thereon information for sterilization cycle;

performing an instrument recall routine for an recalled sterilization cycle in dependence on sterilization cycle parameters for the recalled sterilization cycle, performing the instrument recall routine comprising:

identifying one or more patients for whom an item in the recalled sterilization cycle was used by comparing sterilization cycle parameters for the recalled sterilization cycle to a plurality of records of an instrument usage database, wherein each record of the instrument usage database comprises a number of fields, wherein the fields of the record of the instrument usage database comprise a date of sterilization identifying a date upon which a sterilization cycle was performed, a sterilizer ID identifying a sterilizer used in the sterilization cycle, a load ID identifying a load on the date of sterilization of the sterilization cycle, a number of items sterilized in the load, a patient name identifying a patient for whom an item in the sterilization cycle was used, and a date of use identifying a date upon which the item in the sterilization cycle was used; and initiating a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

21. A computer-implemented method of performing an instrument recall, wherein the method is performed by a controller comprising a processor and a memory coupled to the processor, the controller coupled to a sterilizer and a printer, the method comprising:

receiving first sterilization cycle data for the sterilization cycle, the first sterilization cycle data comprising one or more mechanical indicator values for the sterilization cycle;

receiving second sterilization cycle data for the sterilization cycle; and in response to a determination that mechanical indicators and chemical indicator values for the sterilization cycle match predetermined criteria, generating a sterilization record in accordance with the first sterilization cycle data and second sterilization cycle data, storing the sterilization record in a sterilization database, and printing a sterilization label having printed thereon information for sterilization cycle;

performing an instrument recall routine for an recalled sterilization cycle in dependence on sterilization cycle parameters for the recalled sterilization cycle, performing the instrument recall routine comprising:

identifying one or more patients for whom an item in the recalled sterilization cycle was used by comparing sterilization cycle parameters for the recalled sterilization cycle to a plurality of records of an instrument usage database; and initiating a patient notification routine comprising at least one of outputting of identifying information of the one or more patients for whom an item in the recalled sterilization cycle was used and notifying the one or more patients for whom an item in the recalled sterilization cycle was used about the recalled sterilization cycle.

* * * * *